US007141655B2

(12) United States Patent  
Ebright et al.

(10) Patent No.: US 7,141,655 B2
(45) Date of Patent: Nov. 28, 2006

(54) REAGENTS AND PROCEDURES FOR HIGH-SPECIFICITY LABELING

(75) Inventors: Richard H. Ebright, North Brunswick, NJ (US); Yon W. Ebright, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 503 days.

(21) Appl. No.: 10/461,224

(22) Filed: Jun. 13, 2003

(65) Prior Publication Data

US 2004/0019104 A1 Jan. 29, 2004

Related U.S. Application Data

(60) Provisional application No. 60/388,699, filed on Jun. 14, 2002.

(51) Int. Cl.
- *C07K 1/13* (2006.01)
- *G01N 21/64* (2006.01)
- *C07D 209/10* (2006.01)
- *C07D 263/54* (2006.01)
- *C07D 277/62* (2006.01)

(52) U.S. Cl. ............ 530/402; 436/172; 436/800; 530/408; 530/409; 530/410; 548/102; 548/402

(58) Field of Classification Search ............ 530/402, 530/408, 409, 410; 548/102, 402; 436/172, 436/800
See application file for complete search history.

(56) References Cited

U.S. PATENT DOCUMENTS

| 4,981,977 | A | 1/1991 | Southwick et al. |
| 5,627,027 | A | 5/1997 | Waggoner |
| 5,932,474 | A | 8/1999 | Tsien et al. |

(Continued)

FOREIGN PATENT DOCUMENTS

EP 0747448 A2 5/1996

(Continued)

OTHER PUBLICATIONS

Ratnakar B. Mujumdar et al. *Cyanine Dye Labeling Reagents: Sulfoindocyanine Succinimidyl Esters*, Bioconjugate Chemistry, vol. 4, No. 2, pp. 105-111, Mar./Apr. 1993.

(Continued)

*Primary Examiner*—Mary E. Ceperley
(74) *Attorney, Agent, or Firm*—Hoffmann &Baron, LLP

(57) ABSTRACT

A molecule with two pendant phenylarsine moieties according to the general structural Formula (I) and tautomers, acids, and salts thereof:

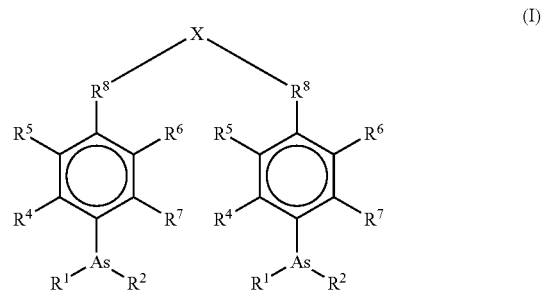

wherein: (i) $R^1$ or $R^2$, are each independently $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

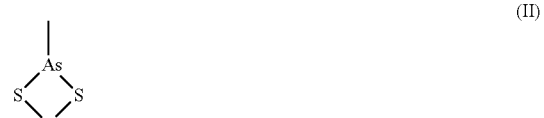

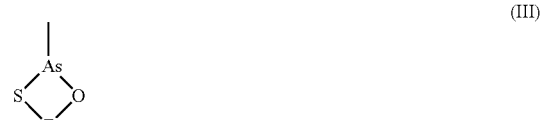

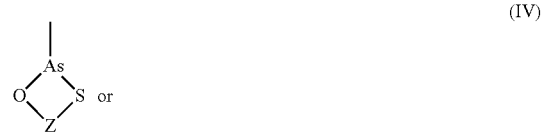

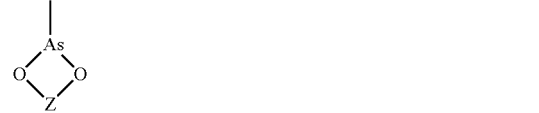

wherein $R^3$ is H, $CH(OH)CH_2OH$, or $(CH_2)_q$—Y, with q being 1–4 and Y being H, OH, $NH_2$, SH, COOH, OAc, $CONH_2$ or CN, and Z represents a hydrocarbon chain comprising 2–4 singly or doubly bonded carbon atoms each of which may be further substituted with one or more of hydrogen, methyl, ethyl, 1-propyl, 2-propyl, methoxy, hydroxy, amino, carboxy, sulfo, oxo, thio, halo (fluoro, chloro, bromo, or fluoro) and $(CH_2)_{n''}SO_3$, wherein n" is 1 or 2; (ii) $R^4$, $R^5$, $R^6$ and $R^7$ are each independently H, F, $OR^3$, $R^3$, OAc, $NH_2$, $N(C_1–C_4$ alkyl$)_2$, $R^1$; or $R^4$ with $R^5$, or $R^6$ together with $R^7$, or both, form a ring; (iii) $R^8$ is a linear or branched optionally substituted spacer having a minimum length of approximately 1.5 and a maximum length of approximately 15 Ångstroms; and (iv) X is a detectable group. Methods of using the bis-phenylarsine molecule also are provided.

19 Claims, 1 Drawing Sheet

U.S. PATENT DOCUMENTS

| | | | |
|---|---|---|---|
| 6,008,378 | A | 12/1999 | Tsien et al. |
| 6,054,271 | A | 4/2000 | Tsien et al. |
| 6,086,737 | A | 7/2000 | Patonay et al. |
| 6,130,094 | A | 10/2000 | Waggoner et al. |
| 6,133,445 | A | 10/2000 | Waggoner et al. |
| 6,197,928 | B1 | 3/2001 | Tsien et al. |
| 6,225,050 | B1 | 5/2001 | Waggoner |

FOREIGN PATENT DOCUMENTS

| | | |
|---|---|---|
| EP | 0747700 B1 | 5/1996 |

OTHER PUBLICATIONS

Jun Nakanishi et al. *Imaging of Conformational Changes of Proteins with a New Environment-Sensitive Fluorescent Probe Designed for Site-Specific Labeling of Recombinant Proteins in Live Cells, Analytical Chemistry*, vol. 73, No. 13, Jul. 1, 2001, pp. 2920-2928, 2001.

Katarina Stroffekova et al. *The Protein-Labeling Reagent FLASH-EDT$_2$ Binds Not Only to CCXXCC Motifs but also Non-Specifically to Endogenous Cysteine-rich Proteins, European Journal of Physiology*, vol. 442, No. 6, pp. 859-866, Sep. 2001.

Griffin et al. *Specific Covalent Labeling of Recombinant Protein Molecules Inside Live Cells, Science*, vol. 281, pp. 269-272, Jul. 1998.

Kapanidis et al. *Site-Specific Incorporation of Fluorescent Probes into Protein: Hexahistidine-Tag-Mediated Fluorescent Labeling with ($Ni^{2+}$: Nitrilotriacetic Acid)$_n$-Fluorochrome Conjugates, J. Am. Chem. Soc.*, vol. 123, pp. 12123-12125, 2001.

Copy of International Search Report from corresponding International Patent Application No. PCT/US 03/18792, filed Jun. 14, 2002.

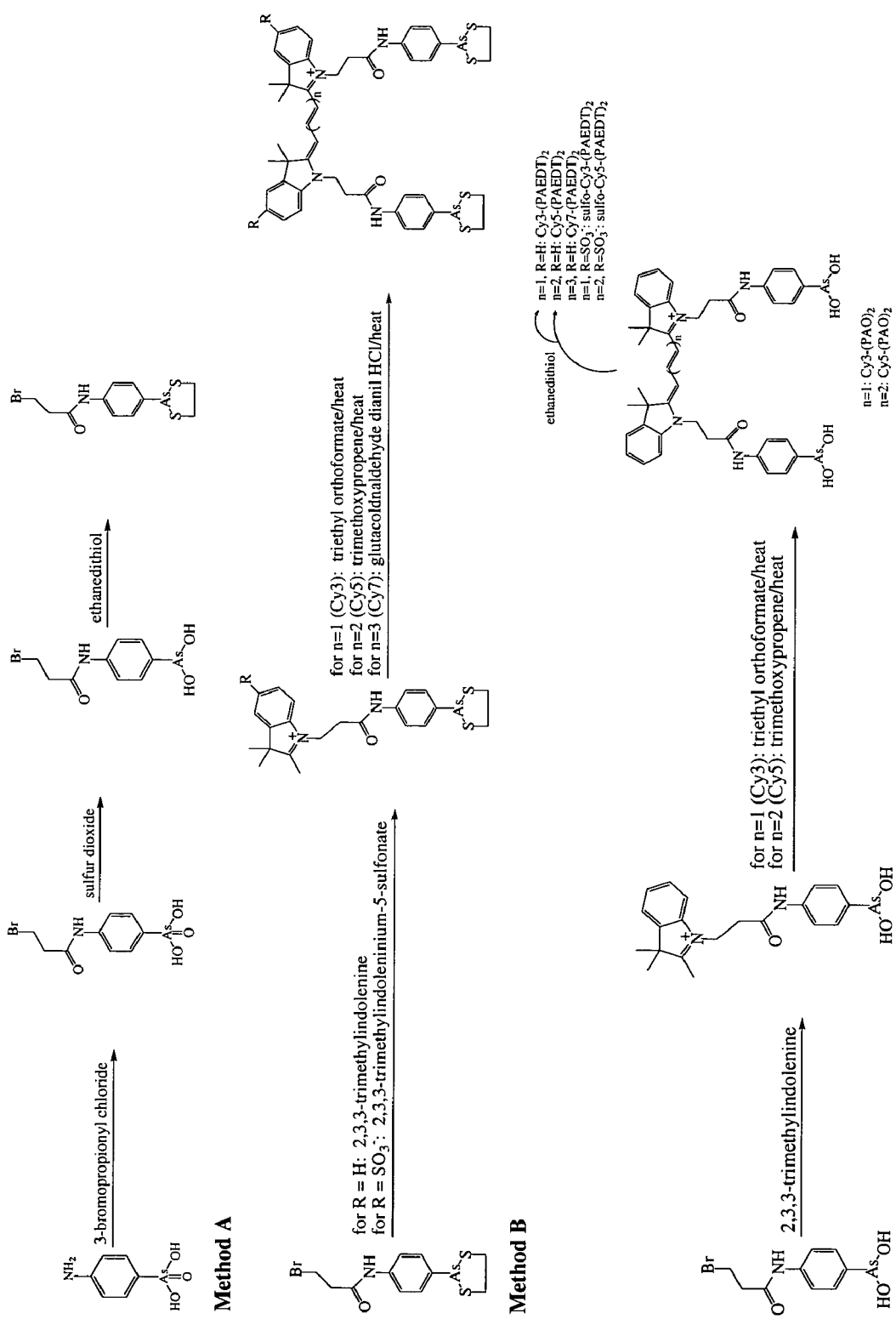

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (3)..(4)
<223> OTHER INFORMATION: Any amino acid at all xaa locations

<400> SEQUENCE: 1

Cys Cys Xaa Xaa Cys Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (3)..(5)
<223> OTHER INFORMATION: Any amino acid at all xaa locations

<400> SEQUENCE: 2

Cys Cys Xaa Xaa Xaa Cys Cys
1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (3)..(6)
<223> OTHER INFORMATION: Any amino acid at all Xaa locations

<400> SEQUENCE: 3

Cys Cys Xaa Xaa Xaa Xaa Cys Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (3)..(7)
<223> OTHER INFORMATION: Any amino acid at all xaa locations

<400> SEQUENCE: 4

Cys Cys Xaa Xaa Xaa Xaa Xaa Cys Cys
1               5

<210> SEQ ID NO 5
<211> LENGTH: 6
<212> TYPE: PRT
<213> ORGANISM: Artificial Sequence
<220> FEATURE:
<223> OTHER INFORMATION: Target sequence.

<400> SEQUENCE: 5

Cys Cys Gly Pro Cys Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Target sequence.

<400> SEQUENCE: 6

Cys Cys Pro Gly Cys Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Target sequence.

<400> SEQUENCE: 7

Cys Cys Gly Pro Gly Cys Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Target sequence.

<400> SEQUENCE: 8
```

```
Cys Cys Pro Gly Pro Cys Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Target sequence.
<220> FEATURE:
<221> NAME/KEY: MISC_FEATURE
<222> LOCATION: (2)..(3)
<223> OTHER INFORMATION: Any amino acid at all xaa locations
<220> FEATURE:
<221> NAME/KEY: MISC_FEATURE
<222> LOCATION: (6)..(7)
<223> OTHER INFORMATION: Any amino acid at all xaa locations

<400> SEQUENCE: 9

Cys Xaa Xaa Cys Cys Xaa Xaa Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Target sequence.

<400> SEQUENCE: 10

Cys Gly Pro Cys Cys Gly Pro Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Target sequence.

<400> SEQUENCE: 11

Cys Pro Gly Cys Cys Pro Gly Cys
1               5
```

REAGENTS AND PROCEDURES FOR HIGH-SPECIFICITY LABELING

CROSS-REFERENCE TO RELATED APPLICATIONS

This application claims priority to U.S. Provisional Patent Application No. 60/388,699, filed on Jun. 14, 2002, which is herein incorporated by reference in its entirety.

This invention was made with Government support under Grant No. NIH R01-GM41376, awarded by the National Institutes of Health. Therefore, the Government has certain rights in this invention.

FIELD OF THE INVENTION

The present invention provides certain bis-phenylarsine derivatives and derivatives thereof, as well as uses of same in labeling polypeptides and other molecules modified to contain target sequences.

BACKGROUND OF THE INVENTION

Characterization of proteins often requires the ability to incorporate detectable groups—e.g., fluorochromes, chromophores, spin labels, radioisotopes, paramagnetic atoms, heavy atoms, haptens, crosslinking agents, and cleavage agents—at specific, defined sites. For proteins that do not contain pre-existing cysteine residues, site-specific labeling can be accomplished by use of site-directed mutagenesis to introduce a cysteine residue at the site of interest, followed by cysteine-specific chemical modification to incorporate the labeled probe. However, for proteins that contain pre-existing cysteine residues, site-specific labeling is difficult. Multiple strategies have been reported: (i) intein-mediated labeling ("expressed protein ligation"), (Muir, et al., *Proc. Natl. Acad. Sci. USA*, 95:6705–6710 (1998)); (ii) transglutaminase-mediated labeling (Sato et al., *Biochem.* 35:13072–13080 (1996)); (iii) oxidation-mediated labeling (Geoghegan, et al., *Bioconj. Chem.*, 3:138–146 (1992)); (iv) transition-metal-chelate-mediated labeling (Kapanidis et al., *J. Amer. Chem. Soc.*, 123:12123 (2001)); and (v) trivalent-arsenic-mediated labeling (Griffin et al., *Science* 281:269–272, 1998) (U.S. Pat. No. 6,008,378). Strategies (i)–(iii) do not permit in situ labeling (i.e., direct labeling of proteins in cuvettes, gels, blots, or biological samples—without the need for a subsequent purification step) or in vivo labeling (i.e., direct labeling of proteins in living cells). Strategy (iv) does not permit labeling and analysis at sub-nanomolar concentrations. Strategy (v) requires a structural scaffold presenting two trivalent-arsenic atoms in a precisely defined spatial relationship and therefore relates only to a limited number of detectable groups (such as those having a xanthene, xanthanone, or phenoxazine structural nucleus).

There is a need for improved methods and compositions for protein labeling. In particular, there is a need for methods and compositions that permit in situ labeling, that permit in vivo labeling, that permit labeling and analysis at sub-nanomolar concentrations, and that encompass a wide range of detectable groups with different properties.

SUMMARY OF THE INVENTION

The invention provides a molecule with two pendant phenylarsine moieties according to the general structural Formula (I) including tautomers, salts, and acids thereof:

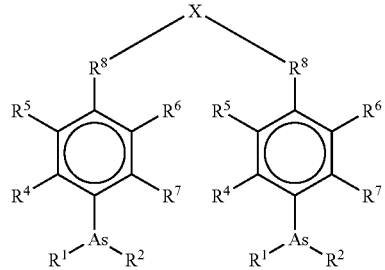

(I)

wherein:

(i) each $R^1$ or $R^2$, independently, is $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

(II)

(III)

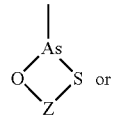 or (IV)

(V)

wherein $R^3$ is H, $CH(OH)CH_2OH$, or $(CH_2)_q$—Y, wherein q is 1–4 and Y is H, OH, $NH_2$, SH, COOH, OAc, $CONH_2$ or CN;

and Z represents a hydrocarbon chain comprising 2–4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thio, halo (fluoro, chloro, bromo, or fluoro) and $(CH_2)_{n''}SO_3$, wherein n'' is 1 or 2;

(ii) $R^4$, $R^5$, $R^6$ and $R^7$ are each independently H, F, $OR^3$, $R^3$, OAc, $NH_2$, $N(C_1-C_4\ alkyl)_2$, $R^1$; or $R^4$ with $R^5$, or $R^6$ together with $R^7$, or both, form a ring;

(iii) $R^8$ is a linear or branched optionally substituted spacer having a minimum length of approximately 1.5 and a maximum length of approximately 15 Ångstroms; and (iv) X is a detectable group.

Furthermore, provided herein is a molecule with two pendant phenylarsine moieties according to the following general structural formulae:

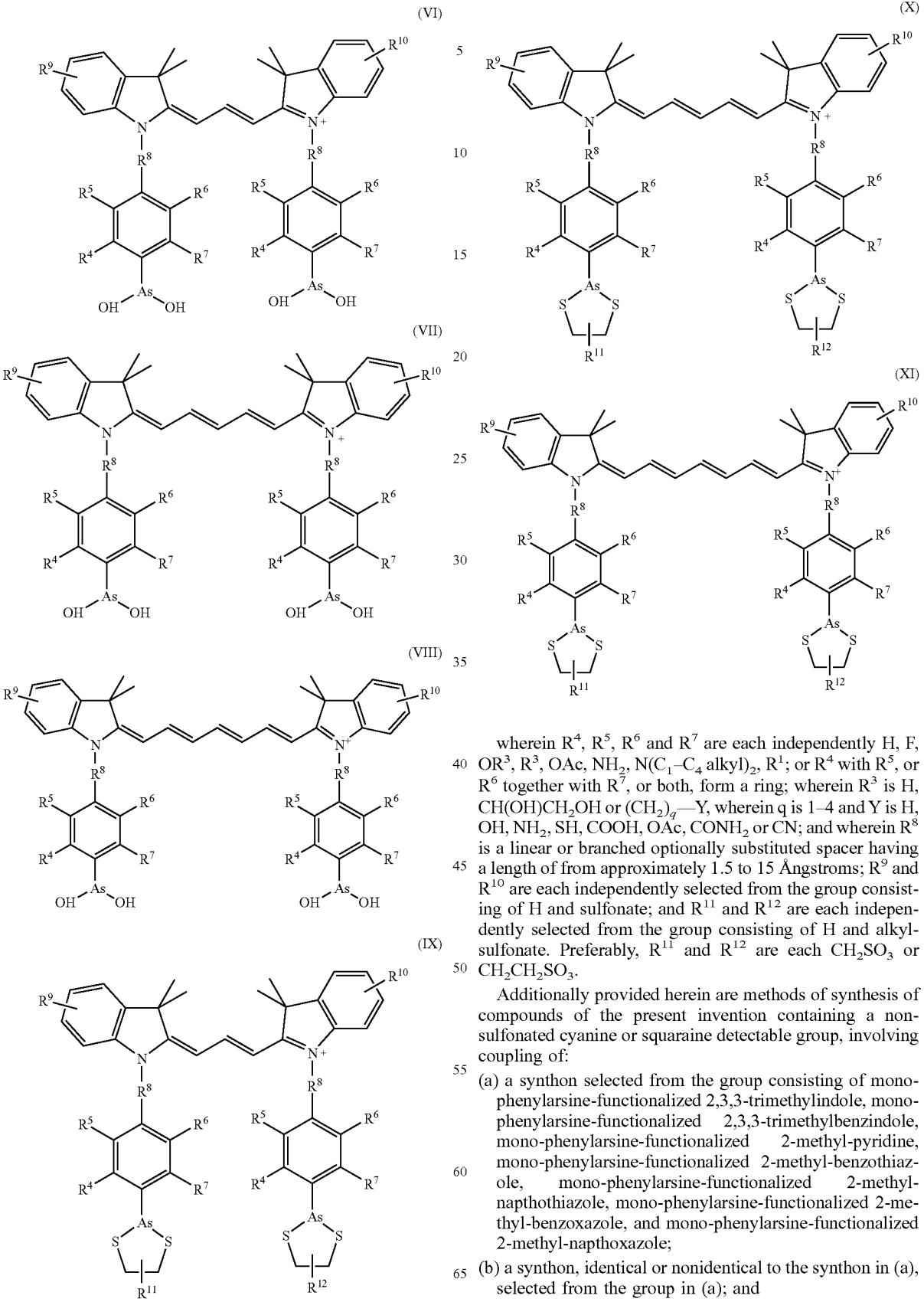

wherein $R^4$, $R^5$, $R^6$ and $R^7$ are each independently H, F, $OR^3$, $R^3$, OAc, $NH_2$, $N(C_1-C_4$ alkyl$)_2$, $R^1$; or $R^4$ with $R^5$, or $R^6$ together with $R^7$, or both, form a ring; wherein $R^3$ is H, $CH(OH)CH_2OH$ or $(CH_2)_q$—Y, wherein q is 1–4 and Y is H, OH, $NH_2$, SH, COOH, OAc, $CONH_2$ or CN; and wherein $R^8$ is a linear or branched optionally substituted spacer having a length of from approximately 1.5 to 15 Ångstroms; $R^9$ and $R^{10}$ are each independently selected from the group consisting of H and sulfonate; and $R^{11}$ and $R^{12}$ are each independently selected from the group consisting of H and alkyl-sulfonate. Preferably, $R^{11}$ and $R^{12}$ are each $CH_2SO_3$ or $CH_2CH_2SO_3$.

Additionally provided herein are methods of synthesis of compounds of the present invention containing a non-sulfonated cyanine or squaraine detectable group, involving coupling of:

(a) a synthon selected from the group consisting of mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;

(b) a synthon, identical or nonidentical to the synthon in (a), selected from the group in (a); and (c) a synthon containing at least one carbon atom.

Additionally provided herein are methods of synthesis of compounds of the present invention containing a di-sulfonated cyanine or squaraine detectable group, involving coupling of:
(a) a synthon selected from the group consisting of mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-6-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole;
(b) a synthon, identical or nonidentical to the synthon in (a), selected from the group in (a); and
(c) a synthon containing at least one carbon atom.

Additionally provided herein are methods of synthesis of compounds of the present invention containing a mono-sulfonated cyanine or squaraine detectable group, involving coupling of:
(a) a synthon selected from the group consisting of mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;
(b) a synthon selected from the group consisting of mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-6-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole; and
(c) a synthon containing at least one carbon atom.

Coupling of the synthons referred to herein can be accomplished in a single step, or in two steps. For example, for symmetric compounds (i.e., where (a) and (b) are identical), coupling of reactants (a), (b) and (c) is desirably carried out in a single reaction step as, for example, set forth in the Examples herein. For asymmetric compounds (i.e., where (a) and (b) are non-identical), coupling the reactants (a), (b) and (c) is desirably carried out in a two step reaction: i.e., reaction of (a) with (c), followed by reaction of the resultant product with (b); or, alternatively, reaction of (b) with (c), followed by reaction of the resultant product with (a).

Additionally provided herein is a labeled target material including a target sequence of the form: $C(X)_iC(X)_jC(X)_kC$, wherein C is cysteine, X is any amino acid, and i, j, and k are each independently 0 or an integer of from 1 to 6, and wherein the target sequence is bonded with a molecule according to Formula (I). In certain preferred embodiments the target sequence is of the form $CC(X)_jCC$ or $CXXC(X)_jCXXC$ more preferably a sequence selected from SEQ ID NOS. 1 to 11.

Also included is a detectable complex including a molecule according to Formula (I) and a target sequence, bonded thereto. The target sequence includes an amino acid sequence of the form: $C(X)_iC(X)_jC(X)_kC$, wherein C is cysteine, X is any amino acid, and i, j, and k are each independently 0 or an integer of from 1 to 6.

The invention also includes a method for imparting fluorescent properties to a target material, including the step of reacting: (a) the target material having a target sequence of the form $C(X)_iC(X)_jC(X)_kC$, wherein C is cysteine, X is any amino acid, and i, j, and k are each independently 0 or an integer of from 1 to 6, with (b) a molecule according to Formula (I), under conditions sufficient to permit bis-phenylarsine moieties of the molecule according to Formula (I) to bond to the target sequence.

Furthermore, provided herein is a method for detecting at least one target material of interest, including the steps of: (a) providing a target material having a target sequence of the form: $C(X)_iC(X)_jC(X)_kC$, wherein C is cysteine, X is any amino acid, and i, j, and k are each independently 0 or an integer of from 1 to 6; (b) incubating the target material with a molecule according to Formula (I), having a detectable group, for a time period sufficient to allow labeling of the target material; and (c) detecting the detectable group, thereby detecting the target material.

Additionally, a method for determining the localization, concentration or interactions of at least one target material of interest on or within a cell, tissue, organ or organism is provided, including the steps of: (a) providing a cell, tissue, organ, or organism containing a target material having a target sequence of the form: $C(X)_iC(X)_jC(X)_kC$, wherein C is cysteine, X is any amino acid, and i, j, and k are each independently 0 or an integer of from 1 to 6; (b) contacting the cell, tissue, organ or organism with a molecule according to Formula (I) having a detectable group for a time period sufficient to allow labeling of the target material; and (c) detecting the detectable group, thereby imaging the localization, concentration or interactions of the target material of interest.

Furthermore, provided herein is an assay method for monitoring a binding process including the steps of: (a) reacting a first component of a specific binding pair with a second component of the pair, with the first component being labeled with a molecule according to Formula (I) having a detectable group; and (b) monitoring the reaction by monitoring a change in a signal of the detectable group.

Also provided herein is an assay method for monitoring a binding process including the steps of: (a) reacting a first component of a specific binding pair with a second component of the pair, with the first component being labeled with a molecule according to Formula (I) having a detectable group; and (b) monitoring the reaction by monitoring at least one of a fluorescence-emission intensity, a fluorescence lifetime, a fluorescence polarization, a fluorescence anisotropy, and a fluorescence correlation of the detectable group.

Additionally provided herein is an assay method for monitoring a binding process, including the steps of: (a) reacting a first component of a specific binding pair with a second component of the pair, with the first component being labeled with a molecule according to Formula (I) wherein X of Formula (I) is a fluorochrome, and with the second component containing Z, wherein Z is one of a fluorochrome and a chromophore, Z being able to participate in fluorescence energy transfer, fluorescence quenching, or exciton formation with X; and (b) monitoring the reaction by monitoring a fluorescent property of X.

The invention also provides an assay method for monitoring a binding process, including the steps of: (a) reacting a first component of a specific binding pair with a second component of the pair, with the first component being labeled with a molecule according to Formula (I) wherein X of Formula (I) is selected from the group consisting of a fluorochrome and a chromophore, and with the second component containing Z, wherein Z is a fluorochrome able to participate in fluorescence energy transfer, fluorescence quenching, or exciton formation with X; and (b) monitoring the reaction by monitoring a fluorescent property of Z.

The invention further provides an assay method for monitoring a reaction, including the steps of: (a) reacting a first participant in a reaction with a second participant in the reaction, the first participant being labeled with a molecule according to Formula (I); and (b) monitoring the reaction by monitoring a change in a detectable property of the detectable group.

Furthermore, provided herein is a method for isolating at least one target material of interest including the steps of: (a) contacting at least one molecule according to Formula (I) immobilized on a solid support, with a solution containing a target material of interest, the target material including a target sequence of the form: $C(X)_iC(X)_jC(X)_kC$, wherein C is cysteine, X is any amino acid, and i, j, and k are each independently 0 or an integer of from 1 to 6, under conditions that allow binding of the target material to immobilized molecules of Formula (I); and (b) eluting the target material with a low-molecular weight monothiol or low-molecular-weight dithiol.

The invention also includes a method for immobilizing at least one target material of interest including the steps of: (a) contacting at least one molecule according to Formula (I) immobilized on a solid support, with a solution containing a target material, the target material containing a target sequence of the form $C(X)_iC(X)_jC(X)_kC$, wherein C is cysteine, X is any amino acid, and i, j, and k are each independently 0 or an integer of from 1 to 6, under conditions that allow binding of the target material to the immobilized molecules according to Formula (I).

The invention also includes a method of screening a library of candidate peptides and identifying a cysteine-containing peptide that binds to a molecule according to Formula (I), the method including the steps of: (a) incubating the molecule of Formula (I) with a peptide library, wherein the library comprises a multiplicity of solid supports, each solid support bearing a single species of peptide, under conditions that permit formation of a complex between the molecule according to Formula (I) and a peptide including a target sequence; and (b) detecting the detectable group, thereby identifying a solid support bearing a species of peptide that binds said molecule of Formula (I).

Furthermore, provided herein is a method of screening a library of peptides and identifying a cysteine-containing peptide that binds to a molecule according to Formula (I), the method including the steps of: (a) introducing the molecule of Formula (I) having a detectable group to a peptide library, wherein the library includes a multiplicity of candidate peptides arrayed on a surface; and (b) identifying a location on the surface having a peptide thereon that binds the molecule of Formula (I) by detecting the detectable group.

The invention also includes a method of screening a library of peptides and identifying a peptide that binds to a molecule according to Formula (I), including the steps of: (a) contacting molecules of Formula (I) immobilized on a solid support with a peptide library, wherein the library comprises a multiplicity of particles, each particle containing a single species of peptide and also containing a nucleic acid that encodes at least one amino acid of the peptide. Optionally, the method further includes isolating a peptide-containing, nucleic-acid-containing particle that binds to the immobilized molecules according to Formula (I); and determining or inferring the sequence of part or all of the nucleic acid associated with the particle, thereby defining the sequence of part or all of the peptide associated with the particle.

Additionally provided herein is a kit including: (a) a molecule according to Formula (I); and (b) a molecule containing a target sequence including an amino acid sequence of the form: $C(X)_iC(X)_jC(X)_kC$, wherein C is cysteine, X is any amino acid, and i, j, and k are each independently 0 or an integer of from 1 to 6.

Further provided herein is a kit including: (a) a molecule according to Formula (I); and (b) a reagent that promotes the formation of a complex between the molecule according to Formula (I) and a peptide having a target sequence of the form: $C(X)_iC(X)_jC(X)_kC$, wherein C is cysteine, X is any amino acid, and i, j, and k are each independently 0 or an integer of from 1 to 6.

BRIEF DESCRIPTION OF THE DRAWINGS

FIG. 1 depicts methods for synthesizing certain bis arsenical molecules according to the invention referred to herein as $Cy3-(PAEDT)_2$; $Cy5-(PAEDT)_2$; $sulfo-Cy7-(PAEDT)_2$; $sulfo-Cy3-(PAEDT-)_2$; and $sulfo-Cy5-(PAEDT)_2$.

DETAILED DESCRIPTION OF THE INVENTION

Compositions of the Invention

The invention provides bis-phenylarsine derivatives having the general chemical Formula (I) and tautomers, acids, and salts thereof:

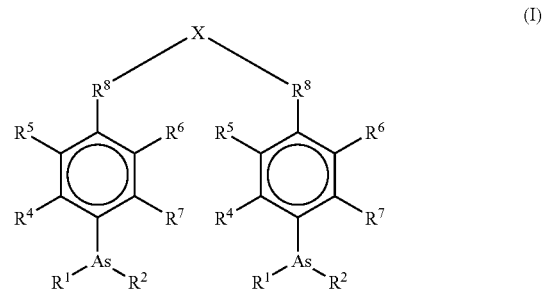

wherein:
(i) each $R^1$ or $R^2$, independently, is $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

-continued

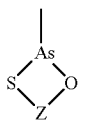
(III)

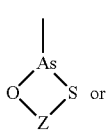
(IV)

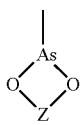
(V)

wherein R³ is H, CH(OH)CH₂OH, or (CH₂)$_q$—Y, wherein q is 1–4 and Y is H, OH, NH₂, SH, COOH, OAc, CONH₂ or CN; and Z represents a saturated or unsaturated hydrocarbon chain comprising 2–4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thio, halo (fluoro, chloro, bromo, or fluoro) and (CH₂)$_{n''}$SO₃, wherein n" is 1 or 2;

(ii) R⁴, R⁵, R⁶ and R⁷ are each independently H, F, OR³, R³, OAc, NH₂, N(C₁–C₄ alkyl)₂, R¹; or R⁴ together with R⁵, or R⁶ together with R⁷, or both, form a ring;

(iii) R⁸ is a linear or branched spacer having a minimum length (when fully extended) of about 1.5, preferably 2.5, more preferably 3.5, and most preferably 4.5 Ångstroms and having a maximum length (when fully extended) of about 15, preferably 12.5, more preferably 10, and most preferably 7.5 Ångstroms; and (v) X is a detectable group.

In one embodiment, R⁸ comprises a chain having a minimum length of 1, preferably 2, and more preferably 3 non-hydrogen atoms and having a maximum length of 9, preferably 8, and more preferably 7 non-hydrogen atoms. Some examples of chains include —(CH₂)$_{1-7}$—C(O)NH— preferably —(CH₂)₂—C(O)NH—.

X in Formula (I) is a detectable group. "Detectable group" as used herein refers to any chemical moiety that can be detected. Examples of detectable groups include fluorescent moieties, phosphorescent moieties, luminescent moieties, absorbent moieties, photosensitizers, spin labels, radioisotopes, isotopes detectable by nuclear magnetic resonance, paramagnetic atoms, heavy atoms, haptens, crosslinking agents, cleavage agents, and combinations thereof.

In one embodiment, X is detected by monitoring a signal. Some signals which may be monitored due to the presence of a detectable group include, for example, fluorescence (fluorescence emission intensity, fluorescence lifetime, fluorescence polarization, fluorescence anisotropy, or fluorescence correlation), luminescence, phosphorescence, absorbance, singlet-oxygen production, electron spin resonance, radioactivity, nuclear magnetic resonance, and X-ray scattering.

In another embodiment, X is detected by receptor-binding, protein-protein or protein-nucleic acid crosslinking, or protein or nucleic acid cleavage.

Preferred detectable groups include fluorescent moieties. In one preferred embodiment, cyanine fluorescent moieties are used. These include, but are not limited to: Cy3: 1-R-2-[3-[1-R-1,3-dihydro-3,3-dimethyl-5-sulfo-2H-indol-2-ylidene]-1-propenyl]-3,3-dimethyl-5-sulfo-3H-indolium, Cy5: 1-R-2-[5-[1-R-1,3-dihydro-3,3-dimethyl-5-sulfo-2H-indol-2-ylidene]-1,3-pentadienyl]-3,3-dimethyl-5-sulfo-3H-indolium, Cy7: 1-R-2-[7-[1-R-1,3-dihydro-3,3-dimethyl-5-sulfo-2H-indol-2-ylidene]-1,3,5-heptatrienyl]-3,3-dimethyl-5-sulfo-3H-indolium, indocyanine green and IRDye (1-R-2-[2-[2-R'-3-[(1-R-1,3-dihydro-3,3-dimethyl-5-sulfo-2H-indol-2-ylidene)ethylidene]-1-cyclohexen-1-yl]ethenyl]-3, 3-dimethyl-5-sulfo-3H-indolium), and mono- and non-sulfonated derivatives thereof. In another preferred embodiment, squaraine fluorescent moieties are used.

Examples of the dyes discussed above are described, inter alia, in Southwick et al., 1990, *Cytometry* 11:418–430; Mujumdar et al., 1993, *Bioconjugate Chemistry* 4:105–111; Waggoner and Ernst, *Fluorescent Regents for Flow Cytometry, Part* 1: *Principles of Clinical Flow Cytometry* (1993) and Haugland, *Molecular Probes Handbook of Fluorescent Probes and Research Chemicals, Molecular* Inc. 6$^{th}$ edition (1996) and Berling and Reiser, *Methoden der Organischer Chemie*, p 231–299 (1972), Oswald et al., *Analytical Biochemistry* 280: 272–277 (2000), Oswald et al. *Photochemistry and Photobiology* 74(2): 237–245 (2001), Oswald et al. *Bioconjugate Chemistry* 10: 925–931 (1999), U.S. Pat. No: 6,086,737. The dye structures in these publications are all incorporated herein by reference.

In a particularly preferred embodiment, X may be selected from the following cyanine detectable groups:

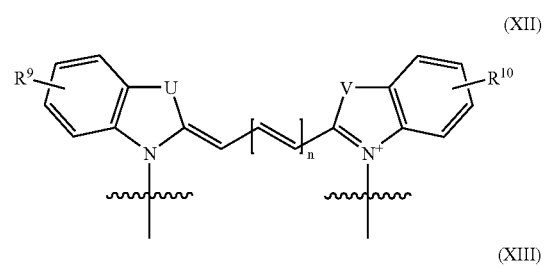
(XII)

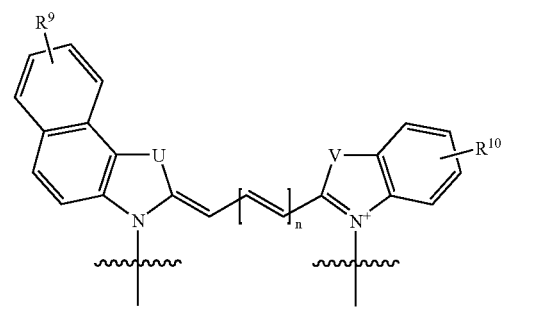
(XIII)

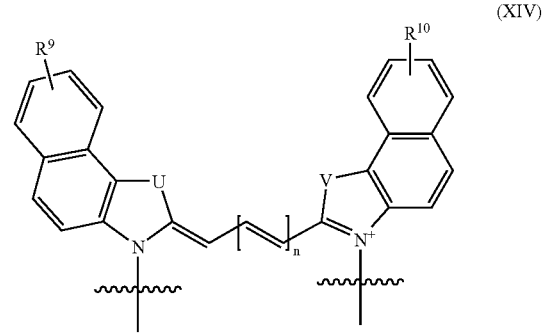
(XIV)

(XV)
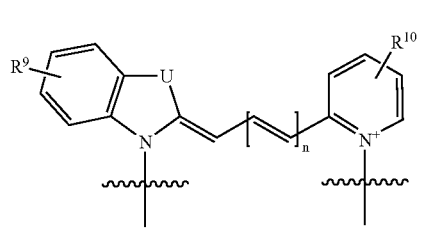
(XVI)
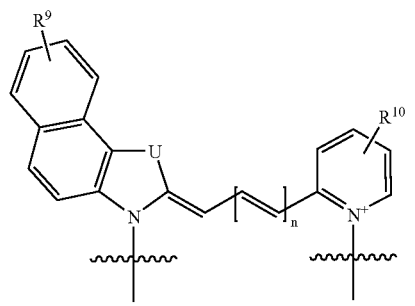
wherein U and V are each independently $C(R^{14})_2$, NH, O, S, or $(CH)_2$; $R^9$ and $R^{10}$ are each independently H or sulfonate; $R^{14}$ is H, $CH_3$, $CH_2CH_3$, or $(CH_2)_2CH_3$; and n is 0 or an integer of from 1 to 6.
In another particularly preferred embodiment, X may be selected from the following squaraine detectable groups:
(XVII)
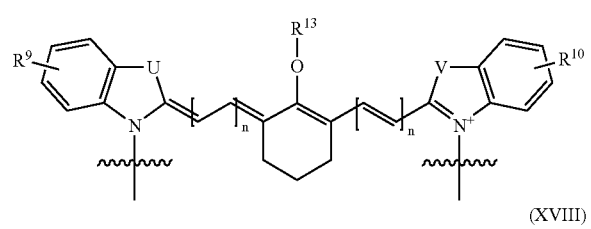
(XVIII)
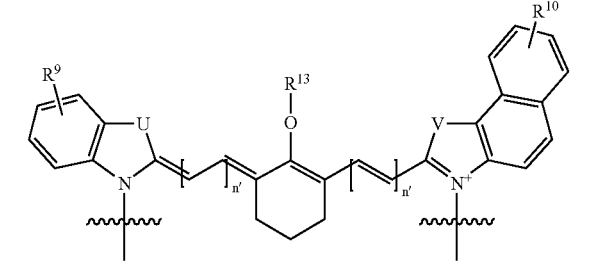
(XIX)
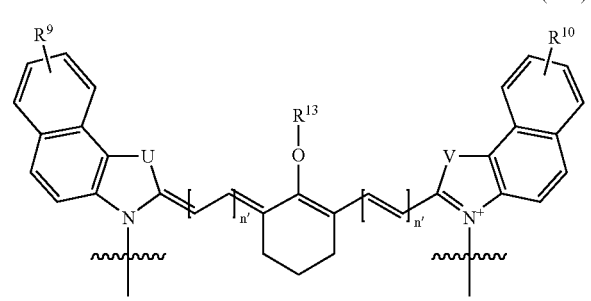
(XX)
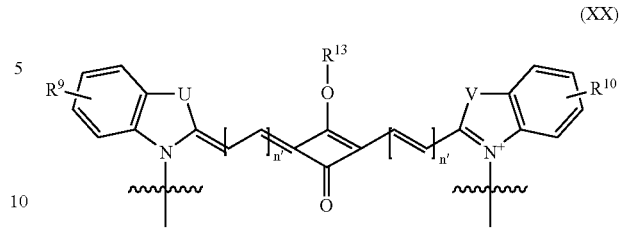
(XXI)
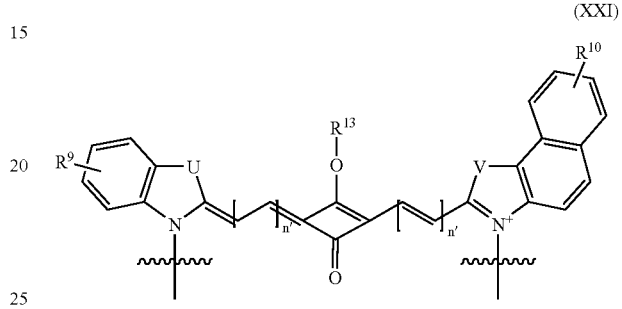
(XXII)
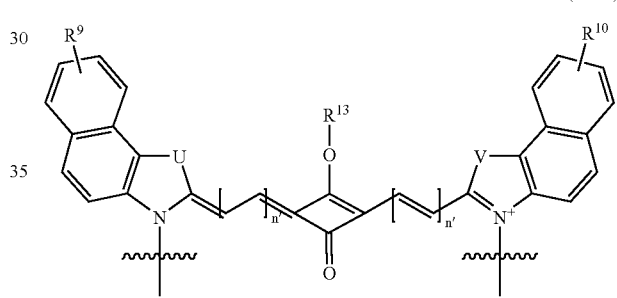
(XXIII)
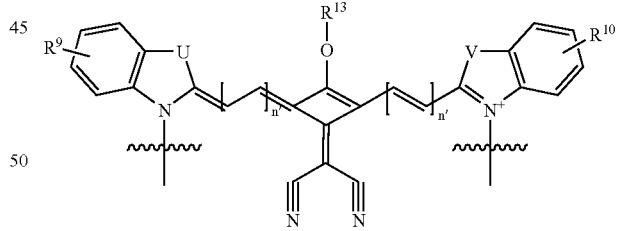
(XXIV)
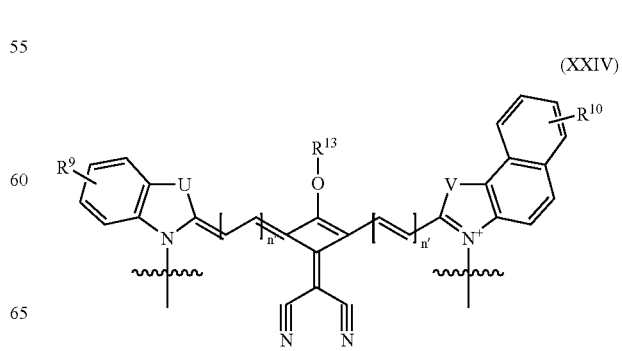

(XXV)

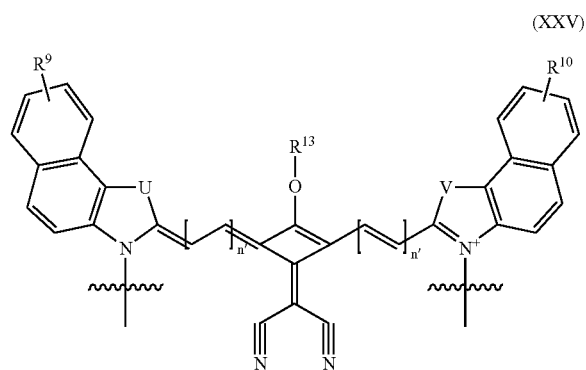

wherein U and V are each independently $C(R^{14})_2$, NH, O, S, or $(CH)_2$; $R^9$ and $R^{10}$ are each independently H or sulfonate; and $R^{13}$ is absent or is selected from the group consisting of H, an alkyl group, and an aryl group; $R^{14}$ is H, $CH_3$, $CH_2CH_3$, or $(CH_2)_2CH_3$; and n' is 0 or an integer of from 1 to 3.

Among the preferred bis-phenylarsine molecules of the present invention are those represented by the following general structural formulae:

(VI)

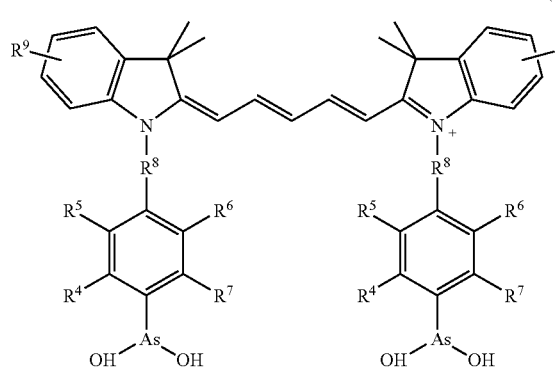

(VII)

(VIII)

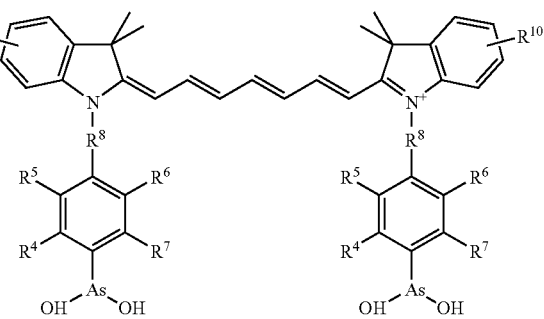

(IX)

(X)

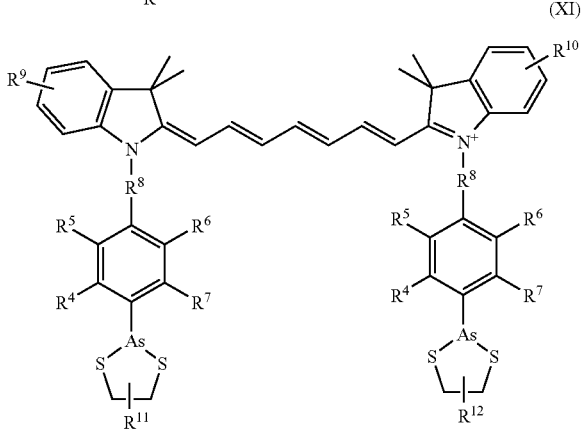

(XI)

wherein $R^4$, $R^5$, $R^6$ and $R^7$ are each independently H, F, $OR^3$, $R^3$, OAc, $NH_2$, $N(C_1-C_4$ alkyl$)_2$, or $R^4$ with $R^5$, or $R^6$ together with $R^7$, or both, form a ring; wherein $R^3$ is H, $CH(OH)CH_2OH$ or $(CH_2)_q$—Y, wherein q is 1–4, and Y is H, OH, $NH_2$, SH, COOH, OAc, $CONH_2$ or CN; and wherein $R^8$ is a linear or branched optionally substituted spacer having a length from about 1.5 to about 15 Ångstroms; $R^9$ and $R^{10}$ are each independently selected from the group consisting of H and sulfonate; and $R^{11}$ and $R^{12}$ are each independently selected from the group consisting of H and alkylsulfonate. Preferably, $R^{11}$ and $R^{12}$ are each $CH_2SO_3$ or $CH_2CH_2SO_3$.

Modifying groups that aid in the use of the bis-phenylarsine derivative may also be incorporated. For example, the bis-phenylarsine derivative may be substituted at one or more positions to add a solid-phase binding group or a crosslinking group.

For applications involving labeling of target materials within living cells, the bis-phenylarsine derivative preferably is capable of traversing a biological membrane. Smaller molecules are generally able to traverse a biological membrane better than larger derivatives. Bis-phenylarsine derivatives of less than 2000 Daltons are preferable for membrane traversal.

The polarity of the bis-phenylarsine derivative can also determine the ability of the bis-phenylarsine derivative to traverse a biological membrane. Generally, a hydrophobic bis-phenylarsine derivative is more likely to traverse a biological membrane. The presence of polar groups can reduce the likelihood of a molecule to traverse a biological membrane. A bis-phenylarsine derivative that is unable to traverse a biological membrane may be further derivatized by addition of groups that enable or enhance the ability of the molecule to traverse a biological membrane. Preferably, such derivatization does not significantly alter the ability of the bis-phenylarsine derivative to subsequently react with a target sequence. The bis-phenylarsine derivative may also be derivatized transiently. In such instances, after traversing the membrane, the derivatizing group is eliminated to regenerate the original bis-phenylarsine derivative. Examples of derivatization methods that increase membrane traversability include ether formation with acyloxyalkyl groups. For example, an acetoxymethyl ether is readily cleaved by endogenous mammalian intracellular esterases. Jansen, A. and Russell, T. J., *J. Chem. Soc.*, 2127–2132 (1965). Also, pivaloyl ester is useful in this regard. Madhu et al., *J. Occul. Pharmaco. Ther.*, 14:389–399 (1998).

Methods of Synthesis of Compositions of the Invention

The invention provides methods of synthesis of compounds of the present invention containing a non-sulfonated cyanine or squaraine detectable group, involving coupling of:

(a) a synthon selected from mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;

(b) a synthon, identical or nonidentical to the synthon in (a), selected from the group in (a); and (c) a synthon containing at least one carbon atom.

The invention provides methods of synthesis of compounds of the present invention containing a di-sulfonated cyanine or squaraine detectable group, involving coupling of:

(a) a synthon selected from mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-5-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole;

(b) a synthon, identical or nonidentical to the synthon in (a), selected from the group in (a); and (c) a synthon containing at least one carbon atom.

The invention provides methods of synthesis of compounds of the present invention containing a mono-sulfonated cyanine or squaraine detectable group, involving coupling of:

(a) a synthon selected from mono-phenylarsine-functionalized 2,3,3-trimethylindole, mono-phenylarsine-functionalized 2,3,3-trimethylbenzindole, mono-phenylarsine-functionalized 2-methyl-pyridine, mono-phenylarsine-functionalized 2-methyl-benzothiazole, mono-phenylarsine-functionalized 2-methyl-napthothiazole, mono-phenylarsine-functionalized 2-methyl-benzoxazole, and mono-phenylarsine-functionalized 2-methyl-napthoxazole;

(b) a synthon selected from mono-phenylarsine-functionalized 2,3,3-trimethyl-5-sulfanato-indole, mono-phenylarsine-functionalized 2,3,3-trimethyl-6-sulfanato-benzindole, mono-phenylarsine-functionalized 2-methyl-5-sulfanato-pyridine, mono-phenylarsine-functionalized 2-methyl-6-sulfanato-benzothiazole, mono-phenylarsine-functionalized 2-methyl-6-sulfanato-napthothiazole, mono-phenylarsine-functionalized 2-methyl-5-sulfanato-benzoxazole, and mono-phenylarsine-functionalized 2-methyl-6-sulfanato-napthoxazole; and (c) a synthon containing at least one carbon atom.

Coupling of the synthons referred to herein can be accomplished in a single step, or in two steps. For example, for symmetric compounds (i.e., where (a) and (b) are identical), coupling of the reactants (a), (b), and (c) desirably is carried out in a single step. For asymmetric compounds (i.e., where (a) and (b) are non-identical), coupling of reactants (a), (b), and (c) desirably is carried out in two steps: i.e., reaction of (a) with (c), followed by reaction of the resultant product with (b); or, alternatively, reaction of (b) with (c), followed by reaction of the resultant product with (a).

Coupling of the synthons referred to herein can be performed in solution, or with one or more synthons attached to a solid support.

Coupling of the synthons referred to herein can be performed with the phenylarsine moiety in an unprotected form, or with the chelator in a protected form initially and optionally deprotected thereafter.

Target Materials and Target Sequences of the Invention

The invention provides detectable complexes of molecules according to Formula (I) with target sequences. Detectable complexes as used herein refer to the association between target amino acid sequences and bis-phenylarsine molecules according to the invention.

Suitable target materials include, but are not limited to: polypeptides, and polypeptide mimetics (such as peptide nucleic acid). Preferably, the target material is a polypeptide.

As used herein, "polypeptide" refers to both short chains, commonly referred to as "peptides, "oligopeptides," or "oligomers," and to longer chains, generally referred to as "proteins." Polypeptides may contain amino acids other than the 20 gene-encoded amino acids. Polypeptides may include amino acid sequences modified either by natural processes, such as post-translational processing, or by chemical modification techniques which are well-known in the art. Such modifications are well described in basic texts and in more detailed monographs, as well as in research literature. Thus "polypeptide" includes peptides, oligopeptides, polypeptides and proteins, all of which terms are used interchangeably herein.

The bis-phenylarsine moieties of the molecules according to Formula (I) bond with a target material containing, or derivatized to contain, at least one copy of a tetracysteine-containing target sequence, herein referred to interchangeably as a "target sequence" or a "tag." The As atoms of the bis-phenylarsine moieties bond with S atoms of the target sequence.

The target material contains, or is modified to contain, at least one copy of a target sequence. The target sequence is generally of the form $C(X)_iC(X)_jC(X)_kC$, wherein C is cysteine, X is any amino acid, i, j and k are each independently 0 or an integer of from 1 to 6. In one preferred embodiment, the target sequence is of the form $CCX_jCC$, more preferably SEQ ID NO:1, SEQ ID NO:2, SEQ ID NO:3, OR SEQ ID NO:4, and even more preferably the sequence is SEQ ID NOS: 5 to 8. In another preferred embodiment, the target sequence is of the form: $CXXC(X)_j CXXC$, more preferably, SEQ ID NO:9, and even more preferably, the sequence is SEQ ID NO:10 or SEQ ID NO:11.

The target sequence may be incorporated at any desired site, or set of sites, within a target material, but preferably is incorporated at a site that is (a) accessible and (b) not essential for structure and function of the target material.

For example, when the target material is a protein, the target sequence preferably is incorporated at the N-terminal region, at the C-terminal region, at an internal loop region, at a surface-exposed non-essential loop, at an internal linker region, or at combinations thereof. The specific site, or set of sites, can be chosen to accommodate the functional requirements of a protein. For example, it is known that N-terminal modification of chemokines can affect their activity; therefore, in applications with chemokines, either C-terminal modification or internal modification would be preferable. Since labeling is performed at defined, user-selected sites, effects on the activity of target material can be avoided. When it is important to preserve the activity of the tagged target material, specific activity testing of the tagged vs. the untagged target material may be conducted to verify activity. See, for example, Mas et al,. *Science*, 233:788–790 (1986).

Target-sequence-containing polypeptides may be generated by total synthesis, partial synthesis, in vitro translation, or in vivo bacterial, archaeal, or eukaryotic production.

In one preferred embodiment, the target sequences and/or target-sequence-containing polypeptides used in the invention are prepared using solid-phase synthesis (see, e.g., Merrifield et al. *J. Am. Chem. Soc.*, 85:2149, (1962) Steward and Young, *Solid Phase Peptides Synthesis*, Freeman, San Francisco, (1969), and Chan and White, *Fmoc Solid Phase Peptide Synthesis—A Practical Approach*, Oxford Press (2000)).

In another preferred embodiment, the target sequences and/or target-sequence-containing polypeptides used in the invention are prepared using native chemical ligation (Dawson et al., *Science*, 266, 1994).

In an especially preferred embodiment, the target sequences and/or target-sequence-containing polypeptides are generated by in vivo bacterial, archaeal, or eukaryotic expression of a recombinant nucleic acid sequence encoding the target-sequence-containing polypeptide. Methods for the construction of recombinant nucleic acid sequences encoding a tag-containing polypeptide are well known in the art (Sambrook and Russel, *Molecular Cloning A Laboratory Manual*, 3$^{rd}$ Ed., Cold Spring Harbor Laboratory, New York (2001), the entirety of which is herein incorporated by reference. In addition, techniques for transient or stable introduction of recombinant nucleic acid sequences into living cells (see, for example, Ausubel et al., *Current Protocols In Molecular Biology*, John Wiley & Sons, Inc. (1995)), for replacement of native nucleic acid sequences by recombinant nucleic acid sequences in living cells (see, for example, Ausubel et al., *Current Protocols In Molecular Biology*, John Wiley & Sons, Inc. (1995)), and for expression of recombinant nucleic acid sequences in living cells (see e.g., Lee and Arthans, H. J. *Biol. Chem.*, 263:3521, (1988); Rosenberg, et al., *Gene*, 56:125 (1987)), are well known in the art.

Labeling is accomplished by contacting a bis-phenylarsine derivative with a target-sequence-containing target material. The bis-phenylarsine derivative may be contacted with a target-sequence-containing target material located, for example, in a test tube, a microtiter-plate well, or immobilized on a solid-phase. Alternatively, the bis-phenylarsine derivative may be contacted with a target-sequence-containing target material located within a cell, tissue, organ, or organism (in which embodiment, the bis-phenylarsine derivative preferably is capable of traversing an intact biological membrane).

In one preferred embodiment, the bis-phenylarsine molecules according to Formula (I) are used to label target-sequence-containing molecules within living cells. The bis-phenylarsine molecules of this invention may be introduced into cells by diffusion (for bis-phenylarsine derivatives capable of traversing biological membranes) or by microinjection, electroporation, or vesicle fusion (for any bis-phenylarsine derivative). The target-sequence-containing molecules may be introduced into cells by microinjection, electroporation, or vesicle fusion, or by expression of recombinant genes in situ.

In one especially preferred embodiment, a target-sequence-containing protein produced by expression of a recombinant gene within living cells is contacted with a probe of this invention by incubating cells in medium containing the probe. Following labeling, and optionally following further manipulations, cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

USES OF THE COMPOSITIONS OF THE INVENTION

It is contemplated that bis-phenylarsine molecules of the invention may be used in a variety of in vitro and in vivo applications.

The bis-phenylarsine molecules of the invention may be used in numerous standard assay formats, as are well known in the art. Some examples of assay formats include fluorescence emission intensity, fluorescence polarization (FP), fluorescence anisotropy (FA), fluorescence resonance energy transfer (FRET), fluorescence correlation spectroscopy (FCS), fluorescence-activated cell—or particle—sorting (FACS), x/y-fluorescence scanning (FluorImaging), epi-illumination optical microscopy, confocal optical microscopy, total-internal-reflection optical microscopy, absorbance spectroscopy, enzyme-linked immunosorbent assay (ELISA), radioimmunoassay (RIA), scintillation proximity assay (SPA), autoradiography, and assays formats that involve use of biotin or other hapten incorporation to provide a recognition event for binding or immobilization of one or more components.

Some examples, which are intended to be illustrative and not limiting of possible assay formats and applications that could use site specific bis-phenylarsine-labeled target materials, are set forth below.

For example, the bis-phenylarsine derivatives of the present invention may be used to detect and/or quantify a polypeptide of interest containing, or derivatized to contain, a target sequence. The target-sequence-containing polypeptide is incubated with a molecule according to Formula (I) for a time period sufficient to allow labeling thereof. Labeled target-sequence-containing polypeptide optionally may be separated from unbound material before the detection step using any method known in the art, and the detectable group X is detected, thereby detecting the polypeptide of interest. The target-sequence-containing polypeptide may be included in any material, including, but not limited to, cuvettes, microtiter plates, capillaries, flow cells, test tubes, gels, blots, and biological samples.

The invention also provides an assay method for monitoring a binding process. In this method, a first component of a specific reaction pair is labeled with a molecule according to Formula (I) and is reacted with a second component of the pair. The reaction can be monitored by monitoring a change in a signal of the detectable group X.

Examples of specific reaction pairs include, but are not restricted to, antibodies/antigens, hormone/receptor, enzyme/substrate, and protein/analyte.

In a fluorescence-emission-intensity assay, the sample is exposed to light of a first wavelength (able to be absorbed by a fluorescent moiety), and fluorescence-emission intensity is monitored at a second wavelength (emitted by said fluorescent moiety). Fluorescence-emission intensity is dependent on the quantity of the fluorescent moiety and on the local environment of the fluorescent moiety.

A fluorescence-emission-intensity assay to detect and quantify binding between two molecules, molecule 1 and molecule 2, may be configured as follows: A reaction mixture is prepared by combining molecule 1 labeled with fluorescent moiety X according to the current invention and molecule 2. Complex formation results, directly or indirectly, from a change in the local environment of X, and, correspondingly, in a change in the fluorescence emission intensity of X. The progress of the reaction is monitored by observing the change in fluorescence emission intensity of X. Equilibrium association and dissociation constants may be extracted from the concentration-dependence of the reaction.

In a fluorescence-polarization (FP) or fluorescence-anisotropy (FA) assay, a sample is exposed to polarized light of a first wavelength (able to be absorbed by a fluorescent moiety), and fluorescence-emission polarization or anisotropy is monitored at a second wavelength (emitted by said fluorescent moiety). Fluorescence-emission polarization or anisotropy is inversely related to the rotational dynamics, and thus to the size, of the fluorescent moiety (or, if the fluorescent moiety is attached to a molecule or complex, to the rotational dynamics, and thus to the size, of the molecule or complex). FP or FA assays permit detection of reactions that result in changes in size of molecules or complexes, including especially, macromolecule-association and macromolecule-dissociation reactions.

An FP or FA assay to detect and quantify binding between two molecules, molecule 1 and molecule 2, may be configured as follows: A reaction mixture is prepared by combining molecule 1 labeled with fluorochrome X according to the current invention and molecule 2. Complex formation results in formation of a higher-molecular-weight, higher-FP, higher-FA species. The progress of the reaction is monitored by observing the decrease in FP or FA. Equilibrium association and dissociation constants are extracted from the concentration-dependence of the reaction.

A further FP or FA assay may be used to detect and quantify proteolytic activity and may be configured as follows: A reaction mixture is prepared by combining a substrate molecule labeled with fluorochrome X according to the present invention and a sample containing a proteolytic enzyme. Cleavage of the substrate molecule by the proteolytic enzyme results in the production of lower-molecular-weight, lower-FP, lower-FA fragments. The progress of the reaction is monitored by observing the decrease in FP or FA.

Fluorescence resonance energy transfer (FRET) is a physical phenomenon that permits measurement of distance). FRET occurs in a system having a fluorescent probe serving as a donor and a second fluorescent probe serving as an acceptor, where the emission spectrum of the donor overlaps the excitation spectrum of the acceptor. In such a system, upon excitation of the donor with light of the donor excitation wavelength, energy can be transferred from the donor to the acceptor, resulting in excitation of the acceptor and emission at the acceptor emission wavelength. FRET readily can be detected—and the efficiency of FRET readily can be quantified—by exciting with light of the donor excitation wavelength and monitoring emission of the donor, emission of the acceptor, or both. The efficiency of energy transfer, E, is a function of the Förster parameter, $R_o$, and of the distance between the donor and the acceptor, R:

$$E=[1+(R/R_o)^6]^{-1}$$

wherein the Förster parameter (in Ångstroms, Å), is:

$$R_0(\text{in Å})=(0.211\times10^{-5})(n^{-4}Q_{DK}{}^2 J)^{1/6}$$

wherein n is the refractive index of the medium, $Q_D$ is the donor quantum yield in the absence of the acceptor, $\kappa^2$ is the orientation factor relating the donor acceptor transition dipoles, and J is the spectral overlap integral of the donor emission spectrum and the acceptor excitation spectrum.

If one performs FRET experiments under conditions where $R_o$ is constant, measured changes in E permit detection of changes in R, and, if one performs experiments under conditions where $R_o$ is constant and known, the measured absolute magnitude of E permits determination of the absolute magnitude of R.

With fluorochromes and chromophores known in the art, FRET is useful over distances of about 1 nm to about 15 nm, which are comparable to the dimensions of biological macromolecules and macromolecule complexes. Thus, FRET is a useful technique for investigating a variety of biological phenomena that produce changes in molecular proximity.

When FRET is used as a detection mechanism, colocalization of proteins and other molecules can be imaged with spatial resolution beyond the limits of conventional optical microscopy.

A FRET assay to detect and quantify binding between two molecules, molecule 1 and molecule 2, may be configured as follows: A reaction mixture is prepared by combining molecule 1 labeled with a molecule according to Formula (I) where detectable group X is a fluorescent moiety and molecule 2 is labeled with a fluorescent moiety Y or a chrompohore Y, wherein X and Y are able to participate in FRET. Complex formation results in increased proximity between X and Y, and, correspondingly, in increased FRET. The progress of the reaction is monitored by observing the increase in FRET. Equilibrium association and dissociation constants may be extracted from the concentration-dependence of the reaction.

A FRET assay to detect and quantify proteolytic activity may be configured as follows: A reaction mixture is prepared by combining a) a substrate molecule labeled at site 1 with Formula (I) wherein detectable group X is a fluorescent moiety and labeled at site 2 with fluorochrome Y, wherein sites 1 and 2 are on opposite sides of the proteolytic-cleavage site, and wherein X and Y are able to participate in FRET, and b) a sample containing a proteolytic enzyme. Cleavage of the substrate molecule by the proteolytic enzyme results in decreased proximity between X and Y and, correspondingly, in decreased FRET. The progress of the reaction is monitored by observing the decrease in FRET.

A FRET assay to detect conformation change within molecule 1 induced upon interaction with molecule 2, may be configured as follows: A reaction mixture is prepared by combining (a) molecule 1 labeled at one site with fluorochrome X according to the current invention and labeled at another site with fluorochrome Y, wherein X and Y are able to participate in FRET, and (b) molecule 2. Conformation change within molecule 1 induced upon interaction with molecule 2 results in a change in proximity between X and Y, and, correspondingly, a change in FRET. The progress of the reaction is monitored by observing the change in FRET.

A FRET assay to measure the distance between two sites, 1 and 2, within a molecule of interest, may be configured as follows: the molecule of interest is labeled at site 1 with fluorochrome X according to the current invention and is labeled at site 2 with fluorochrome Y, wherein X and Y are able to participate in FRET; fluorescence excitation and emission spectra are collected for X and Y; and the distance, R, is calculated as described supra.

Fluorescence emission intensity, lifetime, polarization, aniosotropy and FRET are further described in the following references: Brand, L. and Johnson, M. L., Eds., *Fluorescence Spectroscopy (Methods in Enzymology, Volume* 278), Academic Press (1997), Cantor, C. R. and Schimmel, P. R., *Biophysical Chemistry Part* 2, W. H. Freeman (1980) pp. 433–465. Dewey, T. G., Ed., *Biophysical and Biochemical Aspects of Fluorescence Spectroscopy*, Plenum Publishing (1991). Guilbault, G. G., Ed., *Practical Fluorescence, Second Edition*, Marcel Dekker (1990). Lakowicz, J. R., Ed., *Topics in Fluorescence Spectroscopy: Techniques (Volume* 1, 1991); *Principles (Volume* 2, 1991); *Biochemical Applications (Volume* 3, 1992); *Probe Design and Chemical Sensing (Volume* 4, 1994); *Nonlinear and Two-Photon Induced Fluorescence (Volume* 5, 1997); *Protein Fluorescence (Volume* 6, 2000), Plenum Publishing.

Fluorescence imaging using epi-illumination, confocal, or total-internal-reflection optical microscopy permits characterization of the quantities, locations, and interactions of fluorochrome-labeled target materials within living cells. All fluorescence observables that can be analyzed in vitro—emission intensity, emission lifetime, fluorescence correlation, FP/FA, and FRET—also can be analyzed in living cells (See Nakanishi et al. *Anal. Chem.* 73:2920–2928 (2001); Maiti, S. et al. *Proc. Natl. Acad. Sci. USA* 94: 11753–11757 (1997); Eigen and Rigler, *Proc. Natl. Acad. Sci. USA* 91:5740–5747 (1994) for example of uses of fluorescence in living cells).

The bis-phenylarsine derivatives of this invention may be used to label target-sequence-containing molecules within living cells. The bis-phenylarsine derivatives of this invention may be introduced into cells by diffusion (for bis-phenylarsine derivatives capable of traversing biological membranes) or by microinjection, electroporation, or vesicle fusion (for any bis-phenylarsine derivative). The target-sequence-containing molecules may be introduced into cells by microinjection, electroporation, or vesicle fusion, or by expression of recombinant genes in situ.

In one especially preferred embodiment, a target-sequence-containing protein produced by expression of a recombinant gene within living cells is contacted with a bis-phenylarsine derivative of this invention by incubating cells in medium containing the bis-phenylarsine derivative. Following labeling, and optionally following further manipulations, the cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

The fluorescent molecules of the present invention also can be used, in vitro or in vivo, in single-molecule fluorescence assays with single-molecule detection, wherein fluorescence emission intensity, fluorescence correlation, FP/FA, or FRET is analyzed from individual single molecules.

The fluorescent molecules of the present invention also can be used, in vitro or in vivo, in fluorescence assays with "multiplex" detection, wherein a plurality of different fluorescent molecules are attached to a plurality of different primary molecules, molecule 1a, 1b, . . . 1n, with each primary molecule being specific for a different secondary component, 2a, 2b, . . . 2n, in order to monitor a plurality of reactions between primary molecules and secondary molecules in a single reaction mixture. According to this method of use, each of the primary molecules is separately labeled with a fluorochrome having a different, distinguishable excitation and/or emission wavelength. The primary molecules are then reacted, as a group, with the secondary molecules, as a group, and fluorescence is monitored at each of different, distinguishable excitation and/or emission wavelengths.

The fact that the present invention is compatible with fluorochromes having different, distinguishable excitation and emission wavelengths (see, e.g., Table 1 for excitation maxima and emission maxima of derivatives of Cy3, Cy5, and Cy7 in Examples), makes the invention particularly important for applications involving multiplex detection.

Most or all of the assays above, in vitro or in vivo, can be adapted for high-throughput screening, using formats, equipment, and procedures apparent to persons skilled in the art.

Examples of fluorochromes and chromophores suitable for use in assays above, in conjunction with the molecules of the invention, are presented in Haugland R. P. *Handbook of Fluorescent Probes and Research Chemicals.* Molecular Probes, sixth edition (1996), ISBN 0-9652240-0-7 (Spence, MTZ, ed). Said fluorochromes and chromophores can be incorporated into polypeptides and other molecules of interest by any suitable method, many of which are well known in the art, including, but not limited to, chemical synthesis, enzymatic synthesis, ribosomal synthesis, chemical ligation, chemical modification, and hapten binding (see Haugland R. P. *Handbook of Fluorescent Probes and Research Chemicals*, supra). Alternatively, fusions of autofluorescent proteins, such as green fluorescent protein, to a polypeptide of interest can be encoded as nucleic-acid fusion constructs, produced in cells, and analyzed in cells or in vitro.

The methods of the invention may be used in many areas of biology and biological research including drug screening, diagnostics and academic research.

It further is contemplated that the bis-phenylarsine molecules of the invention may be used for immobilization and/or affinity-purification of target-sequence-containing molecules.

Immobilization may be accomplished by: (a) covalently attaching a bis-phenylarsine derivative of the invention to a surface or other solid support (via detectable group X or via a linker); (b) contacting the resulting bis-phenylarsine-derivative-containing surface or other solid support with a solution containing a target-sequence-containing target material; and (c) optionally washing the surface or the solid support to remove unbound material.

Affinity purification may be accomplished by: (a) covalently attaching a bis-phenylarsine molecule to a surface or other solid support, (b) contacting the resulting bis-phenylarsine-molecule-containing surface or other solid support with a solution containing a target-sequence-containing molecule, (c) optionally washing the surface or other solid support to remove unbound material, and (d) eluting the target-sequence-containing molecule with a low-molecular-weight monothiol (e.g., β-mercaptoethanol) or, preferably, a low-molecular-weight dithiol (e.g., dithiothreitol or ethanedithiol). The solid support may be, for example, a surface, a bead, a gel, or a chromatographic matrix.

It is also contemplated that the bis-phenylarsine molecules of the invention may be used to screen libraries of target sequences in order to define optimal target sequences. Library construction and/or methods for detection, isolation and identification of peptides can be accomplished according to Lam et al., *Nature*, 354:82–84 (1991) and/or Chen et al., *Methods in Enzymology* 267:211–219 (1996).

In one embodiment, screening of libraries of possible target sequences may be accomplished by: (a) incubating a molecule according to Formula (I) with a peptide library wherein the library comprises a multiplicity of solid supports, each solid support bearing a single species of peptide, under conditions that permit formation of a complex between a molecule according to Formula (I) and a peptide including a target sequence; (b) optionally washing the solid supports to remove unbound material; and (c) detecting the detectable group, thereby identifying a solid support bearing a species of peptide that binds to the molecule of Formula (I).

In another embodiment, screening of libraries of possible target sequences may be accomplished by: (a) introducing the molecule of Formula (I) to a peptide library, wherein the library includes a multiplicity of candidate peptides arrayed on a surface; and (b) detecting the detectable group, thereby identifying a location on the surface having a peptide thereon that binds said molecule of Formula (I).

Alternatively, screening of libraries of possible target sequences may be accomplished by: (a) generating a polysome-, phage-, or cell-displayed combinatorial peptide library; (b) contacting the polysome-, phage-, or cell-displayed combinatorial peptide library with molecules according to Formula (I) immobilized on a surface or other solid support; (c) optionally washing the surface or other solid support to remove unbound material; (d) eluting with low-molecular-weight monothiol or, preferably, low-molecular-weight dithiol; (e) optionally repeating steps b–d one or more times; and (f) identifying target sequence(s) present in eluted material by determining nucleotide sequence(s) encoding target sequence(s) (methods essentially as in Kay et al. *Methods* 24:240–246 (2001); Dower et al. *Curr. Opin. Chem. Biol.* 6:390–398 (2002)).

The invention also provides a kit. The kit includes a molecule according to Formula (I) and a reagent the promotes the formation of a complex between the molecule of Formula (I) and a target sequence of the invention. In one embodiment, the reagent is a monothiol or a dithiol.

The invention also provides a kit including a molecule according to Formula (I) and a peptide including a target sequence of the form: $C(X)_iC(X)_jC(X)_kC$ wherein C is cysteine, X is any amino acid, and i, j, and k are each independently 0 or an integer of from 1 to 6.

It will be apparent that the present invention has been described herein with reference to certain preferred or exemplary embodiments. The preferred or exemplary embodiments described herein may be modified, changed, added to, or deviated from without departing from the intent, spirit and scope of the present invention, and it is intended that all such additions, modifications, amendments and/or deviations be included within the scope of the following claims.

EXAMPLES

The following references are herein incorporated by reference and relate to the examples set forth below:

1. Fisher, N. and Hamer, F., Tricarbocyanines. *J. Chem. Soc.* 189–193 (1933).
2. Mujumdar, et al., R., "Cyanine dye labeling reagents: sulfoindocyanine succinimidyl esters," *Bioconj. Chem.* 4, 105–111 (1993).
3. Mekler, M., et al., "Structural organization of RNA polymerase holoenzyme and the RNA polymerase-promoter open complex: systematic fluorescence resonance energy transfer and distance-constrained docking," *Cell*, 108, 599–614 (2002).
4. Niu, W., "Identification and characterization of interactions between a transcription activator and the transcription machinery," Ph.D dissertation, Rutgers University, New Brunswick, N.J. (1999).
5. Tang, H., et al., "Location, structure, and function of the target of a transcriptional activator protein," *Genes & Dev,* 8:3058–3067 (1995).
6. Kunkel, T. "Rapid and efficient site-specific mutagenesis without phenotypic selection," *Proc. Natl. Acad. Sci. USA* 82, 488–492 (1985).
7. Tang, H., et al., "Rapid RNA polymerase genetics: one-day, no-column preparation of reconstituted recombinant *Escherichia coli* RNA polymerase," *Proc. Natl. Acad. Sci. USA* 92, 4902–4906 (1995).
8. Studier, F., et al., "Use of T7 RNA polymerase to direct expression of cloned genes,: *Methods Enzylomol.* 185, 125–138 (1990).

Example 1

Synthesis of Cy3 bis-propionamido-phenylarsineoxide [Cy3-(PAO)$_2$]

1.1: 4-(bromopropionamido)-phenylarsineoxide

Bromopropionic acid anhydride [formed by reacting bromopropionic acid (1.66 g, 10.86 mmol) with DCC (1.12 g, 5.43 mmol) in 20 ml anhydrous dichloromethane for 15 minutes at 25° C., and filtering off the solid that precipitated] was added to a solution of aminophenylarsineoxide (1 g, 5.43 mmol, synthesized according to published protocol) in 10 ml DMF, and allowed to stir overnight. The amino phenylarsineoxide was rendered soluble by adding to it 10.86 mmol HCl/ether followed by neutralization with triethylamine and filtering the away the solid that formed. The solution was quenched with 20 ml water, and filtered to remove solids. The filtrate was evaporated to an oil, and purified via flash chromatography. In later preparations, 3-bromopropionyl chloride was used instead of the anhydride.

Alternative Preparation:

4-(bromopropionamido)-phenylarsanilic acid

Into 20 ml water was added potassium hydroxide (1 g, 18.4 mmol), p-arsanilic acid (2.04 g, 9.4 mmol), and sodium bicarbonate (3.06 g, 28 mmol). The suspension was stirred until all the solids dissolved. Ice was added to the solution until some ice remained in the solution. Into the icy solution was added 3-bromopropionyl chloride (2.38 g, 13.9 mmol) aliquot-wise over 2 minutes. The solution was vigorously stirred for 5 minutes, then extracted with 10 ml dichloromethane in a separatory funnel. The dichloromethane layer was discarded, the aqueous layer was cooled on ice, and acidified with 50% sulfuric acid until the pH was 1. A white solid precipitated, and was collected via vacuum filtration. Yield: 2.967 g (8.4 mmol, 89% yield). (M+H$^+$): expected, 352, 354; found, 352, 354.

4-(bromopropionamido)-phenylarsineoxide 20 mg of sodium iodide was added to a solution of 4-(bromopropionamido)-phenylarsanilic acid (1 g, 2.84 mmol) in 10 ml methanol and 10 ml 48% hydrobromic acid. Sulfur dioxide was bubbled into the stirred solution for 15 minutes, during which time a white solid precipitated. The gas was removed, and the suspension stirred for another 5 minutes. The solid was collected via vacuum filtration. Yield: 0.75 g, 2.23 mmol, 78% yield.

1.2: 4-(2,33-trimethylindolyl)-propionamido-phenylarsineoxide 4-(Bromopropionamido)-phenylarsineoxide (Example 1.1; 0.23 g, 0.72 mmol) and 2,3,3-trimethylindolenine (Aldrich; 160 mg, 10 mmol) were mixed and heated at 80° C. in a screw-top vial for 6 hours. Upon cooling, the purple mass was triturated with copious diethyl ether. The crude product was used without further purification.

1.3: Cy3 bis-propionamido-phenylarsineoxide [Cy3-(PAO)$_2$]

To 4-(2,33-trimethylindolyl)-propionamido phenylarsineoxide (Example 1.2; 0.72 mmol) was added triethyl orthoformate (Aldrich; 100 µl, 0.68 mmol) and 500 µl pyridine in a screw-cap vial. The mixture was heated at 80° C. for 6 h. Upon cooling, the mixture was triturated with a copious amount of diethyl ether. The solid was collected and purified via flash chromatography (silica, 240–400 mesh, 1–20% MeOH—CHCl$_3$.). Yield: 63 mg. (M+H$^+$): expected, 839.7; found, 839.4. The mass spectrum indicated that the compound was mainly in the arsonous form. Absorbance at 550 nm and 260 nm indicate the presence of the Cy3 moiety and the phenylarsine group.

Example 2

Synthesis of Cy5 bis-propionamido-phenylarsineoxide [Cy5-(PAO)$_2$]

2.1: Cy5 bis-propionamido-phenylarsineoxide [Cy5-(PAO)$_2$]

Into 4-(2,33-trimethylindolyl)-propionamido-phenylarsineoxide (Example 1.2; crude 130 mg, 0.26 mmol) was added 1,3,3-trimethoxypropene (Karl Industries, Inc.; 50 µl, 0.38 mmol) in 400 µl pyridine in a screw-cap vial. The reaction was heated with a heat gun for 3 min, until a turquoise color imparted. Upon cooling, the reaction mixture was triturated with diethyl ether and ethyl acetate. The solid was collected and purified via flash chromatography (silica, 240–400 mesh, 1–20% MeOH—CHCl$_3$.). Yield: 3 mg. M+H$^+$ (after dissolution in methanol in the presence of trace acetic acid): expected, 865.7; found, 921.3 (arsonous methyl ether).

Example 3

Synthesis of Cy3 bis-propionamido-phenylarsine-ethanedithiol [Cy3-(PAEDT)$_2$], method A 3.1: 4-(bromopropionamido)-phenylarsine-EDT 1,2-Ethanedithiol (Aldrich; 25 µl, 0.30 mmol) was added to 4-(bromopropionamido)-phenylarsineoxide (Example 1.1; 100 mg, 0.30 mol) dissolved in 1 ml of hot methanol. After 5 min, a white solid precipitated and was collected. Yield: 63.7 mg, 0.16 mmol, 53%.

3.2: 4-(2,3,3-trimethylindolyl)-propionamido-phenylarsine-EDT 4-(Bromopropionamido)-phenylarsine-EDT (Example 3.1; 34 mg, 0.086 mmol) and 2,3,3-trimethylindolenine (Aldrich; 50 mg, 0.3 mmol) and were mixed and heated at 90° C. in a screw-top vial for 6 hours. Upon cooling, the purple mass was triturated with copious diethyl ether. Yield: 40 mg. The crude product was used without further purification.

3.3: Cy3 bis-propionamido-phenylarsine-ethanedithiol [Cy3-(PAEDT)$_2$]

4-(2,33-trimethylindolyl)-propionamido-phenylarsine-EDT (crude, 19 mg, 0.034 mmol) was suspended in 200 µl pyridine and triethyl orthoformate (50 µl, 0.34 mmol) in a screw cap glass vial. The mixture was heated with a heat gun until the deep violet color of the dye stayed constant. Upon cooling to room temperature, the pyridine was evaporated to yield a deep purple solid. It was dissolved in 1 ml methanol and precipitated with ether to yield 23 mg of crude product. FIG. 1, method A depicts the method of synthesis of Cy3-(PAEDT)$_2$.

Example 4

Synthesis of Cy3 bis-propionamido-phenylarsine-ethanedithiol [Cy3-(PAEDT)$_2$], method B 4.1: Cy3 bis-propionamido-phenylarsine-ethanedithiol [Cy3-(PAEDT)$_2$]

Into a solution of Cy3-(PAO)$_2$ (Example 1.3; 300 nmol in 100 μl DMF), was added 1 μl 1,2-ethanedithiol (Aldrich, 12 μmol). After 10 min at room temperature, the sample was evaporated under high vacuum (yielding an oil), dissolved in chloroform, and purified via flash chromatography (silica, 240–400 mesh, 1–20% MeOH—CHCl$_3$.). Yield: 220 nmol, 73%. (M+H$^+$): expected, 955.2; found, 955.4. FIG. 1, method B depicts this method of synthesis of Cy3-(PAEDT)$_2$.

Example 5

Synthesis of Cy5 bis-propionamido-phenylarsine-ethanedithiol [Cy5-(PAEDT)$_2$], method A 5.1: Cy5 bis-propionamido-phenylarsine-ethanedithiol; Cy5-(PAEDT)$_2$ 4-(2,33-trimethylindolyl)-propionamido-phenylarsine-EDT (crude, 17 mg, 0.031 mmol) was suspended in 200 μl pyridine and 1,3,3-trimethoxypropene (50 μl, 0.38 mmol) in a screw cap glass vial. The mixture was heated with a heat gun until the deep blue color of the dye stayed constant. Upon cooling to room temperature, the pyridine was evaporated to yield a deep blue solid. It was redissolved in 1 ml chloroform and purified using silica chromatography (straight chloroform followed by gradual increase of methanol to 10% methanol). Yield: 7.26 mg, 8.15 μmol, 54%. (M+H$^+$): expected, 981.13; found, 981.3. FIG. 1, method A depicts this method of synthesis of Cy5-(PAEDT)$_2$.

Example 6

Synthesis of Cy5 bis-propionamido-phenylarsine-ethanedithiol [Cy5-(PAEDT)$_2$], method B 6.1: Cy5 bis-propionamido-phenylarsine-ethanedithiol; Cy5-(PAEDT)$_2$ Into a solution of Cy5-(PAO)$_2$ (Example 1.3; 300 nmol in 100 μl DMF), was added 1 μl 1,2-ethanedithiol (Aldrich, 12 μmol). After 10 min at room temperature, the sample was evaporated under high vacuum (yielding an oil), dissolved in chloroform, and purified via flash chromatography (silica, 240–400 mesh, 1–20% MeOH—CHCl$_3$.). Yield: 108 nmol, 36%. (M+H$^+$): expected, 981.13; found, 981.3. FIG. 1, method B depicts this method of synthesis of Cy5-(PAEDT)$_2$

Example 7

Synthesis of Cy7 bis-propionamido-phenylarsine-ethanedithiol [Cy7-(PAEDT)$_2$]

7.1: Cy7 bis-propionamido-phenylarsine-ethanedithiol; Cy7-(PAEDT)$_2$

Into 4-(2,3,3-trimethylindolyl)-propionamido-phenylarsine-EDT (Example 3.1; 5.5 mg, 10 μmol) was added glutacoldnadehyde dianil HCl (5.68 mg, 20 μmol, synthesized according to Fisher, N. and Hamer, F. "Tricarbocyanines," *J. Chem. Soc.* 189–193 (1933)) in 50 μl pyridine in a screw-cap vial. The reaction mixture was heated with a heat gun for 3 min until a dark blue color appeared. Upon cooling, the reaction mixture was triturated with diethyl ether, dissolved in the smallest volume MeOH and again triturated with diethyl ether. The solid was collected and purified via flash chromatography (silica, 240–400 mesh, 1–10% MeOH—CHCl$_3$.). The slowest green fraction was collected and gave the correct UV-VIS absorbance (270 nm for the phenylarsine-ethanedithiol moiety and 765 nm for Cy7). Yield: 0.16 μmol (3.2%). (M+H$^+$): expected, 1007.2; found, 1007.2.

Example 8

Synthesis of Cy3 bis-sulfonato bis-propionamido-phenylarsine-ethanedithiol [sulfo-Cy3-(PAEDT)$_2$]

8.1: 4-(2,3,3-trimethylindolyl-5-sulfonato)-propionamido-phenylarsine-ethanedithiol 4-(Bromopropionamido)-phenylarsine-EDT (Example 3.1; 50 mg, 0.127 mmol) and the potassium salt of 2,3,3-trimethyl-indoleninium-5-sulfonate (30 mg, 10.8 mmol; synthesized according to Mujumdar, et al., "Cyanine dye labeling reagents: sulfoindocyanine succinimidyl esters," *Bioconj. Chem.* 4, 105–111 (1993)) were suspended in 500 μl dichlorobenzene and heated at 90° C. in a screw-top vial for 6 hours. Upon cooling, the dichlorobenzene was decanted, the solid was triturated with copious diethyl ether, redissolved in the smallest volume of hot methanol, and upon cooling, reprecipitated with ether. Yield: 50 mg. The crude product was used without further purification.

8.2: Cy3 bis-sulfonato bis-propionamido-phenylarsine-ethanedithiol; [sulfo-Cy3-(PAEDT)$_2$]

To 4-(2,3,3-trimethyl-5-sulfoindolyl)-propionamido-phenylarsine-EDT (Example 8.1; crude, 50 mg) was added 200 μl pyridine and triethyl orthoformate (100 μl, 0.67 mmol) in a screw cap glass vial. The mixture was heated with a heat gun until the deep purple color of the dye stayed constant. Upon cooling to room temperature, the pyridine was evaporated to yield a deep purple solid, which was triturated with ether. About 25% of the crude solid was purified by reverse-phase C18 HPLC, and the main peak collected. Yield: 1 mg. (M$^-$): expected, 1114.12; found, 1114.1.

Example 9

Synthesis of Cy5 bis-sulfonato bis-propionamido-phenylarsine-ethanedithiol [sulfo-Cy5-(PAEDT)$_2$]

9.1: Cy5 bis-sulfonato bis-propionamido-phenylarsine-ethanedithiol; [sulfo-Cy5-(PAEDT)$_2$]

To 4-(2,3,3-trimethyl-5-sulfoindolyl)-propionamido-phenylarsine-EDT (Example 8.1; crude, 12 mg) was added 100 μl pyridine and 1,3,3-trimethoxypropene (25 μl, 0.19 mmol) in a screw cap glass vial. The mixture was heated with a heat gun until the deep blue color of the dye stayed constant. Upon cooling to room temperature, the pyridine was evaporated to yield a deep blue solid. The solid was triturated with ether to give 20 mg of a deep blue solid.

Example 10

Synthesis of Cy3 bis-sulfonato bis-propionamido-phenylarsine-propanedithiol-sulfonic acid [sulfo-Cy3-(PAsulfoPDT)$_2$]

10.1: Cy3 bis-sulfonato bis-propionamido-phenylarsine-propanedithiol-sulfonic acid [sulfo-Cy3-(PAsulfoPDT)$_2$]

To sulfo-Cy3-(PAEDT)$_2$ (Example 8.2; 500 nmol in 1 ml DMF) was added 2,3-dimercapto-1-propanesulfonic acid, sodium salt (20 µM in 0.5 ml MeOH). The reaction was allowed to proceed for 1 hour at room temperature, after which solvent was evaporated under high vacuum. The sample was re-dissolved in 2 ml water and desalted using two Sep-Pak C18 cartridges, evaporated, and purified using reversed-phase HPLC on C18. Yield: 500 nmol.

Example 11

Synthesis of Cy5 bis-sulfonato bis-propionamido-phenylarsine-propanedithiol-sulfonic acid [sulfoCy5-(SO$_3$)$_2$-(PAsulfoPDT)$_2$]

11.1: Cy5 bis-sulfonato bis-propionamido-phenylarsine-propanedithiol-sulfonic acid [sulfo-Cy5-(PAsulfoPDT)$_2$]

To sulfo-Cy5-(PAEDT)$_2$ (Example 9.1; 400 nmol in 1 ml DMF) was added 2,3-dimercapto-1-propanesulfonic acid, sodium salt (20 µM in 0.5 ml MeOH). The reaction was allowed to proceed for 1 hour at room temperature, after which solvent was evaporated under high vacuum. The sample was re-dissolved in 2 ml water and desalted using two Sep-pak C18 cartridges, evaporated, and purified using reversed-phase HPLC on C18. Yield: 300 nmole (M$^{2-}$): expected, 663.5; found, 663, 664, 665.

Table 1 depicts the spectroscopic properties of the fluorochrome conjugates described above in methanol. The excitation and emission maxima are listed.

TABLE 1

Spectroscopic Properties of Fluorochrome Conjugates in Methanol

| fluorochrome | $\lambda_{max,\ exc}$ (nm) | $\lambda_{max,em}$ (nm) |
|---|---|---|
| Cy3-(PAO)$_2$ | 552 | 566 |
| Cy3-(PAEDT)$_2$ | 552 | 567 |
| sulfo-Cy3-(PAEDT)$_2$ | 558 | 572 |
| sulfo-Cy3-(PAsulfoPDT)$_2$ | 557 | 570 |
| Cy5-(PAO)$_2$ | 647 | 665 |
| Cy5-(PAEDT)$_2$ | 648 | 666 |
| sulfo-Cy5-(PAEDT)$_2$ | 650 | 673 |
| sulfo-Cy5-(PAsulfoPDT)$_2$ | 652 | 667 |
| Cy7-(PAEDT)$_2$ | 743 | 774 |

Example 12

Site-specific Labeling 12.1: Plasmids Encoding Untagged and Tagged α Derivatives Plasmid pHTf1α-Bam encodes *Escherichia coli* RNA polymerase α subunit under control of the lpp-'lacPUV5 tandem promoter (Mekler et al., *Cell*, 108, 599–614 (2002); Niu, W., Ph.D dissertation, Rutgers University, New Brunswick, N.J. (1999); Tang et al., *Genes & Dev*, 8:3058–3067 (1995)). The following plasmids encoding tetracysteine-tagged α derivatives were constructed by use of site-directed mutagenesis (methods as in Kunkel, *Proc. Natl. Acad. Sci. USA* 82, 488–492 (1985)):

pHTf1α-Bam(CGPCN), encodes α-CGPCN
pHTf1α-Bam(CGPCCGPCN), encodes α-CGPCCGPCN
pHTf1α-Bam(CGPCGCGPCN), encodes α-CGPCGCGPCN
pHTf1α-Bam(CGPCGGCGPCN), encodes α-CGPCGGCGPCN
pHTf1α-Bam(CPGCN), encodes α-CPGCN
pHTf1α-Bam(CPGCCPGCN), encodes α-CPGCCPGCN
pHTf1α-Bam(CPGCGCPGCN), encodes α-CPGCGCPGCN
pHTf1α-Bam(CPGCGGCPGCN), encodes α-CPGCGGCPGCN
pHTf1α-Bam(CCGPCCN), encodes α-CCGPCCN
pHTf1α-Bam(CCPGCCN), encodes α-CCPGCCN
pHTf1α-Bam(CCPGPCCN), encodes α-CCPGPCCN
pHTf1α-Bam(CCGPGCCN), encodes α-CCGPGCCN
pHTf1α-Bam(CCPGPGCCN), encodes α-CCPGPGCCN
pHTf1α-Bam(CCGPGPCCN), encodes α-CCGPGPCCN Plasmid pHTT7f1-NHα encodes *Escherichia coli* RNA polymerase α subunit with an N-terminal hexahistidine tag under control of the bacteriophage T7 gene 10 promoter (Tang et al., *Proc. Natl. Acad. Sci. USA* 92, 4902–4906 (1995)). pHTT7f1-NHα derivatives were constructed by replacing the ClaI-BamHI rpoA segment of plasmid pHTf1T7-NHα with corresponding segments of plasmid pHTf1α-Bam derivatives.

12.2: Labeling of Untagged and Tagged α Derivatives, Crude Cell Lysates

Transformants of *E. coli* strain BL21(DE3) (Novagen; Studier et al., *Methods Enzylomol.* 185, 125–138 (1990)) with pHTT7f1-NHα derivatives were shaken at 37° C. in 10 ml LB containing 2 mg/ml ampicillin until OD$_{600}$=0.7, induced by addition of IPTG to 1 mM, and further shaken for another 3 h at 37° C. Cells were harvested by centrifugation (4,600×g; 5 min, 4° C.), and stored at −80° C. Immediately before use, cells were re-suspended in 600 µl 100 mM Tris-HCl, pH 7.9, 200 mM NaCl, 1 mM β-mercaptoethanol, 1 mM phenylmethylsulfonyl fluoride, 7 µM pepstatin A, and 23 µg/ml lysozyme, incubated 5 min at 4° C., and lysed by sonication. Lysates were cleared by centrifugation (16,000× g; 5 min at 4° C.).

To 100 µl cleared lysate, was added 0, 1, or 10 µl 0.5 M dithiothreitol (DTT), and bis-arsenical Cy3-(PAO)$_2$, Cy3-(PAEDT)$_2$, Cy5-(PAO)$_2$, or Cy5-(PAEDT)$_2$ to 20 µM (added as 2 µl of 1 mM solution in dimethylformamide). Following 20 min at 25° C., 15 µl aliquots were mixed with 5 µl 0.25 M Tris-HCl, pH 6.8, 2% SDS, 0.01% bromophenol blue, and 30% glycerol and analyzed by SDS-PAGE on 4–20% gradient gels (Criterion, Bio-Rad, Inc.), followed by x/y fluorescence scanning (for Cy3: Molecular Dynamics FluorImager 595, with excitation=514 nm and emission>610 nm; for Cy5: Molecular Dynamics Storm 860, with excitation=635 nm and emission>650 nm).

Labeling of tagged a derivatives was specific; thus, in reactions in the presence of 5 mM DTT, fewer than ten other proteins in the cell lysates were labeled detectably, and, in reactions in the presence of 50 mM DTT, only one other protein in the cell lysate was labeled detectably. Labeling of tagged α derivatives was tag-dependent and required specific tetracysteine tags; thus, in reactions in the presence of 5 mM or 50 mM DTT, labeling was observed with α-CCPGCCN, α-CCGPCCN, α-CCPGPCCN, α-CCG-PGCCN, α-CCPGPGCCN, and α-CCGPGPCCN and, to a lesser degree, α-CGPCCGPCN, but no labeling was observed with untagged α, α-CGPCN and α-CPGCN.

12.3: Labeling of Tagged α, Purified Protein

To cleared lysates (1.4 ml prepared as above, but from 50 ml cultures), was added 2.8 µl 1 M imidazole and 0.2 ml $Ni^{2+}$-NTA agarose (Qiagen). Following 15 min at 25° C., samples were transferred to 2 ml columns (Poly-Prep, Bio-Rad, Inc.), washed with 10 ml buffer A (100 mM Tris-HCl, pH 7.9, 200 mM NaCl, 2 mM imidazole, and 5% glycerol), washed with 2 ml buffer A containing 10 mM imidazole, and eluted with 2×1 ml buffer A containing 40 mM imidazole. Samples were dialyzed against 100 mM Tris-HCl, pH 7.9, 200 mM NaCl, 1 mM β-mercaptoethanol, 1 mM DTT, and 5% glycerol. Yield: ~300 µg. Purity: ~85%.

Labeling reactions contained (11 µl): 10 µM α derivative, 450 µM bis-arsenical Cy3-$(PAO)_2$, Cy3-$(PAEDT)_2$, Cy5-$(PAO)_2$, or Cy5-$(PAEDT)_2$, 100 mM Tris-HCl, pH 7.9, 200 mM NaCl, 0.5, 5, or 50 mM DTT, 1 mM β-mercaptoethanol, 9% dimethyformamide, and 5% glycerol. Following 20 min at 25° C., 15 µl aliquots were mixed with 5 µl 0.25 M Tris-HCl, pH 6.8, 2% SDS, 0.01% bromophenol blue, and 30% glycerol and analyzed by SDS-PAGE as described in Example 12.2.

Labeling was tag-dependent; thus, in reactions in the presence of 0.5 mM or 5 mM DTT, labeling was observed with α-CCPGCCN, but no labeling was observed with untagged α.

Example 13

Immobilization/affinity-chromatography 13.1: Immobilization/affinity-chromatography of Untagged and Tagged α Derivatives Cleared lysates (1 ml, prepared as described above, but from 20 ml cultures) were equilibrated with 1 ml phenylarsine oxide agarose (Thiobond resin; Invitrogen, Inc.; re-suspended and charged per manufacturer's procedures) for 30 min at 25° C. with gentle rocking. Samples were transferred to disposable columns (Poly-Prep, Bio-Rad, Inc.), washed with 3×2 ml buffer B (100 mM Tris-HCl, pH 7.9, 200 mM NaCl, 1 mM EDTA, 1 mM β-mercaptoethanol, and 5% glycerol), washed with 3×2 ml buffer B containing 0.5 mM DTT, washed with 3×2 ml buffer B containing 5 mM DTT, and eluted with 3×2 ml buffer B containing 50 mM DTT. Aliquots (20 µl) were analyzed by SDS-PAGE as described in Example 12.2.

Tagged α could be immobilized on phenylarsine oxide agarose in the absence of DTT, could be retained in the presence of 0.5 mM DTT and could be eluted in the presence of 5 and 50 mM DTT resulting in ~10-fold purification α-CCGPCCN and α-CCPGCCN; yield, ~200 µg; purity, >95%). Immobilization and retention was specific; thus, fewer than ten other proteins in the cell lysates were detectably immobilized and retained in the presence of 5 mM DTT. Immobilization was tag-dependent; thus, untagged a could not be retained in the presence of 5 mM DTT.

What is claimed is:

1. A molecule with two pendant phenylarsine moieties according to the general structural Formula (I) and tautomers, acids, and salts thereof:

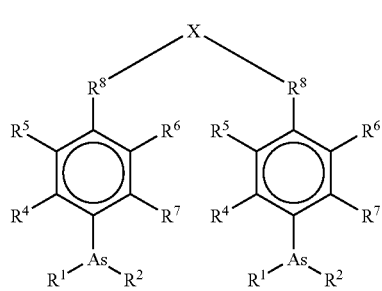

(I)

wherein:

(i) each $R^1$ or $R^2$, independently, is $O^-$, $S^-$, $OR^3$ or $SR^3$ with the provision that if either $R^1$ or $R^2$ is absent, the other remaining group is $=O$ or $=S$; or $R^1$ and $R^2$, together with the arsenic atom, form a ring according to one of the general structural Formulae (II), (III), (IV), or (V):

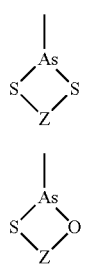

(II)

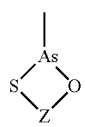

(III)

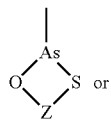

(IV)

or

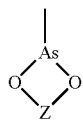 (V)

wherein R³ is H, CH(OH)CH₂OH or (CH₂)$_q$—Y, wherein q is 1–4, and Y is H, OH, NH₂, SH, COOH, OAc, CONH₂ or CN;

and Z represents a hydrocarbon chain comprising 2–4 singly or doubly bonded carbon atoms wherein each carbon atom may be further substituted with one or more groups selected from hydrogen, methyl, ethyl, 1-propyl, 2-propyl, methoxy, hydroxy, amino, carboxy, sulfo, oxo, thiol, halo (fluoro, chloro, bromo, or fluoro), (CH₂)$_{n'}$SO₃—, and (CH₂)$_{n''}$ SO₃H, wherein n" is 1 or 2;

(ii) R⁴, R⁵, R⁶ and R⁷ are each independently H, F, OR³, R³, OAc, NH₂, N(C₁–C₄ alkyl)₂; or R⁴ with R⁵, or R⁶ together with R⁷, or both, form a ring;

(iii) R⁸ is a linear or branched optionally substituted spacer having a minimum length of approximately 1.5 and a maximum length of approximately 15 Ångstroms; and (iv) X is a detectable group, wherein X is a fluorochrome.

2. The molecule according to claim 1, wherein R⁸ has a minimum length of about 3.5 Ångstroms and a maximum length of about 10 Ångstroms.

3. The molecule according to claim 1, wherein R⁸ has a minimum length of about 1 atom and a maximum length of about 9 atoms.

4. The molecule according to claim 1, wherein X is a fluorescent moiety.

5. The molecule according to claim 1, wherein X is derived from a cyanine dye.

6. The molecule according to claim 1, wherein X is derived from a squaraine dye.

7. The molecule according to claim 1, where X is selected from the group consisting of:

a. 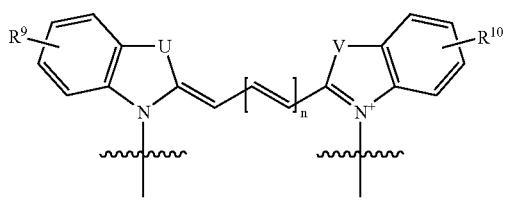 (XII)

b. 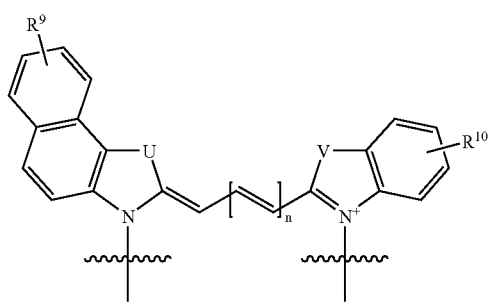 (XIII)

c. 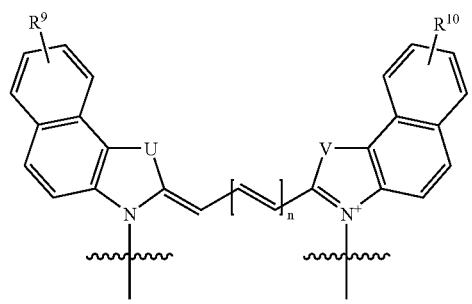 (XIV)

d. 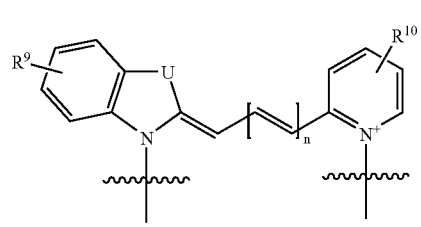 (XV)

e. 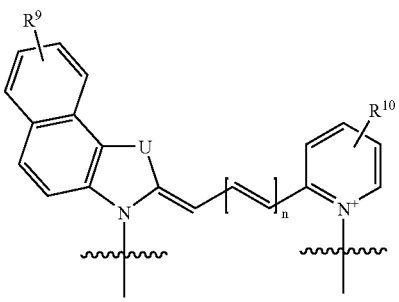 (XVI)

wherein U and V are each independently C(R¹⁴)₂, NH, O, S, or (CH)₂; R⁹ and R¹⁰ are each independently H or sulfonate; R¹⁴ is H, CH₃, CH₂CH₃, or (CH₂)₂CH₃; and n is 0 or an integer of from 1 to 6.

8. The molecule according to claim 1, wherein n is 1, 2 or 3.

9. The molecule according to claim 1, wherein X is selected from the group consisting of:

a. 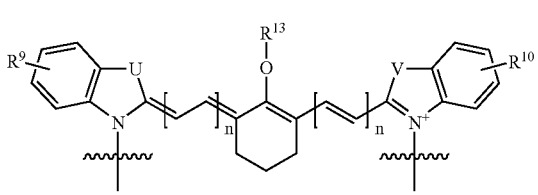 (XVII)

-continued
b. (XVIII)
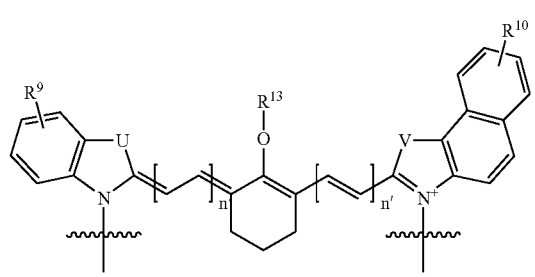
c. (XIX)
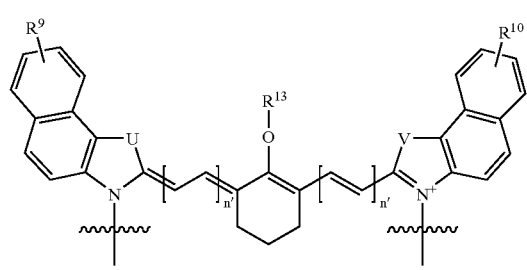
d. (XX)
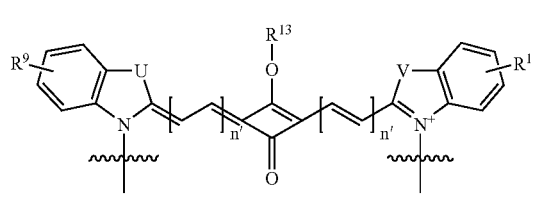
e. (XXI)
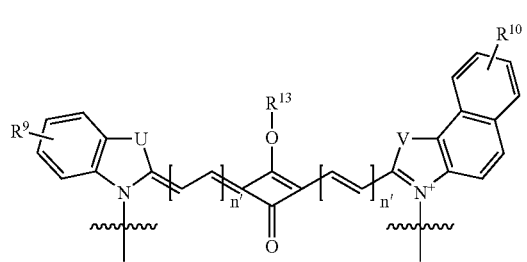
-continued
f. (XXII)
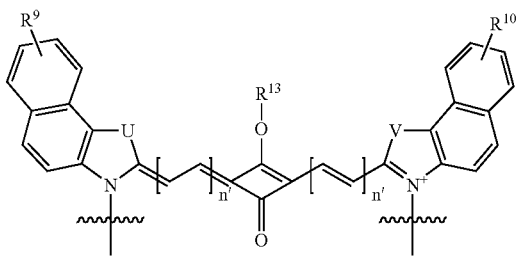
g. (XXIII)
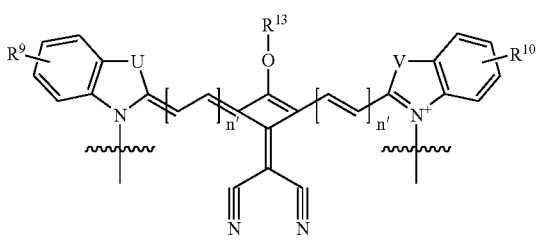
h. (XXIV)
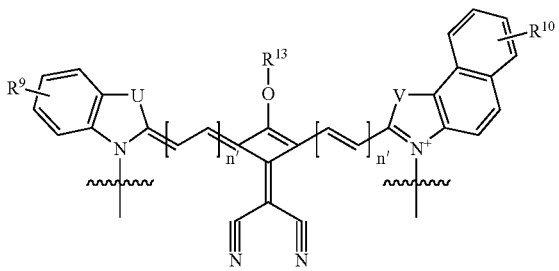
i. (XXV)
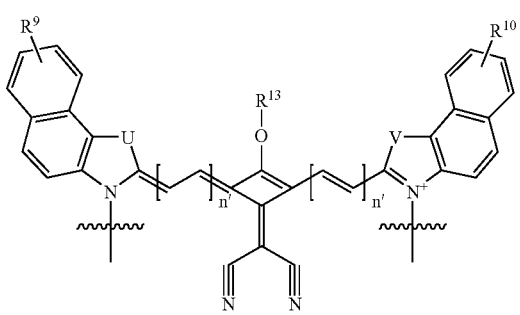

wherein U and V are each independently C(R$^{14}$)$_2$, NH, O, S, or (CH)$_2$; R$^9$ and R$^{10}$ are each independently H or sulfonate; R$^{13}$ is absent or is selected from the group consisting of H, an alkyl group, and an aryl group; R$^{14}$ is H, CH$_3$, CH$_2$CH$_3$, or (CH$_2$)$_2$CH$_3$; and n' is 0 or an integer from 1 to 3.

10. The molecule according to claim 9, wherein n' is 0, 1, or 2.

11. The molecule according to claim 1, wherein said molecule is capable of traversing a biological membrane.

12. A molecule with two pendant phenylarsine moieties according to the general structural Formula (VI):

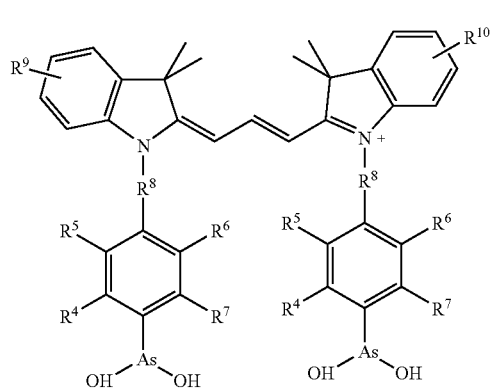

(VI)

wherein R$^4$, R$^5$, R$^6$ and R$^7$ are each independently H, F, OR$^3$, R$^3$, OAc, NH$_2$, or N(C$_1$–C$_4$ alkyl)$_2$; or R$^4$ with R$^5$, or R$^6$ together with R$^7$, or both, form a ring; wherein R$^3$ is H, CH(OH)CH$_2$OH or (CH$_2$)$_q$—Y, wherein q is 1–4 and Y is H, OH, NH$_2$, SH, COOH, OAc, CONH$_2$ or CN; R$^8$ is a linear or branched optionally substituted spacer having a length of from approximately 1.5 to approximately 15 Ångstroms; and R$^9$ and R$^{10}$ are each independently selected from the group consisting of H and sulfonate.

13. A molecule with two pendant phenylarsine moieties according to the general structural Formula (VII):

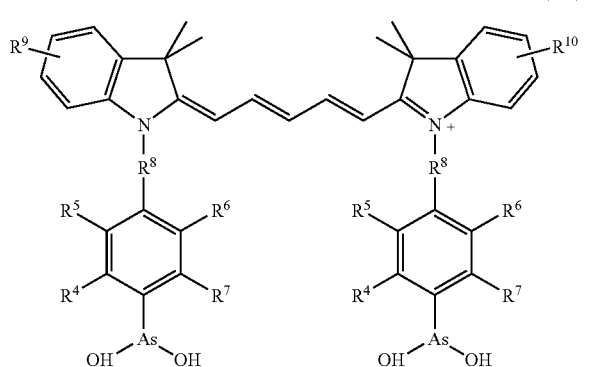

(VII)

wherein R$^4$, R$^5$, R$^6$ and R$^7$ are each independently H, F, OR$^3$, R$^3$, OAc, NH$_2$, N(C$_1$–C$_4$ alkyl)$_2$; or R$^4$ with R$^5$, or R$^6$ together with R$^7$, or both, form a ring; wherein R$^3$ is H, CH(OH)CH$_2$OH or (CH$_2$)$_q$—Y, wherein q is 1–4, and Y is H, OH, NH$_2$, SH, COOH, OAc, CONH$_2$ or CN; and R$^8$ is a linear or branched optionally substituted spacer having a length of from approximately 1.5 to approximately 15 Ångstroms; and R$^9$ and R$^{10}$ are each independently selected from the group consisting of H and sulfonate.

14. A molecule with two pendant phenylarsine moieties according to the general structural Formula (VIII):

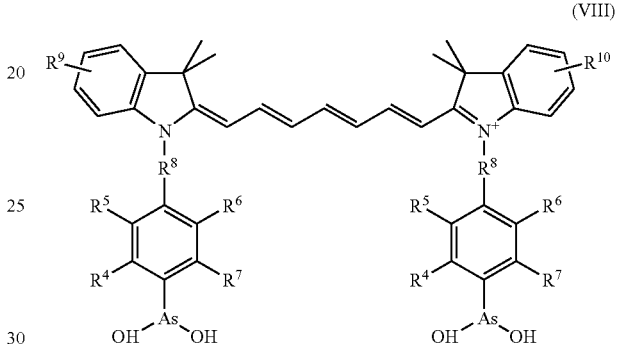

(VIII)

wherein R$^4$, R$^5$, R$^6$ and R$^7$ are each independently H, F, OR$^3$, R$^3$, OAc, NH$_2$, N(C$_1$–C$_4$ alkyl)$_2$; or R$^4$ with R$^5$, or R$^6$ together with R$^7$, or both, form a ring; wherein R$^3$ is H, CH(OH)CH$_2$OH, or (CH$_2$)$_q$—Y, wherein q is 1–4 and Y is H, OH, NH$_2$, SH, COOH, OAc, CONH$_2$ or CN; and R$^8$ is a linear or branched optionally substituted spacer having a length of from approximately 1.5 to approximately 15 Ångstroms; and R$^9$ and R$^{10}$ are each independently selected from the group consisting of H and sulfonate.

15. A molecule with two pendant phenylarsine moieties according to the general structural Formula (IX):

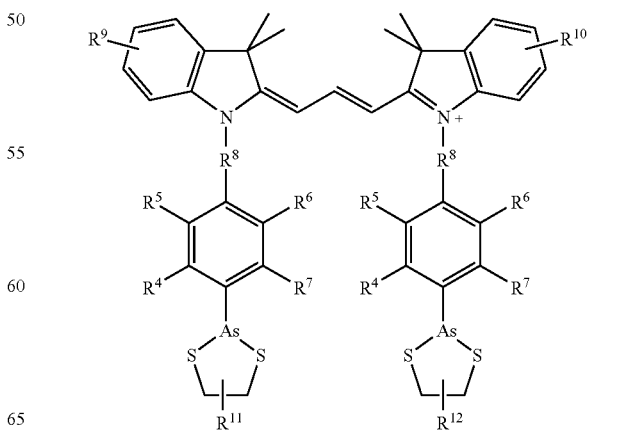

(IX)

wherein R⁴, R⁵, R⁶ and R⁷ are each independently H, F, OR³, R³, OAc, NH₂, N(C₁–C₄ alkyl)₂; or R⁴ with R⁵, or R⁶ together with R⁷, or both, form a ring; wherein R³ is H, CH(OH)CH₂OH or (CH₂)$_q$—Y, wherein q is 1–4 and Y is H, OH, NH₂, SH, COOH, OAc, CONH₂ or CN; R⁸ is a linear or branched optionally substituted spacer having a length of from approximately 1.5 to approximately 15 Ångstroms; R⁹ and R¹⁰ are each independently selected from the group consisting of H and sulfonate; and R¹¹ and R¹² are each independently selected from the group consisting of H, (CH₂)$_{n''}$SO₃—, and (CH₂)$_{n''}$SO₃H, wherein n'' is 1 or 2.

16. A molecule with two pendant phenylarsine moieties according to the general structural Formula (X):

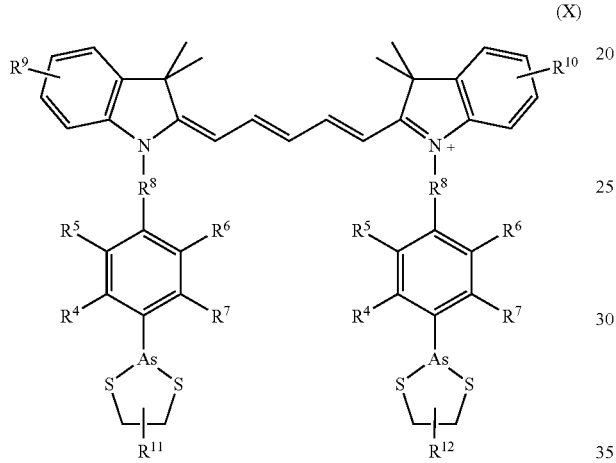

(X)

wherein R⁴, R⁵, R⁶ and R⁷ are each independently H, F, OR³, R³, OAc, NH₂, N(C₁–C₄ alkyl)₂; or R⁴ with R⁵, or R⁶ together with R⁷, or both, form a ring; wherein R³ is H, CH(OH)CH₂OH, or (CH₂)$_q$—Y, wherein q is 1–4 and Y is H, OH, NH₂, SH, COOH, OAc, CONH₂ or CN; R⁸ is a linear or branched optionally substituted spacer having a length of from approximately 1.5 to approximately 15 Ångstroms; R⁹ and R¹⁰ are each independently selected from the group consisting of H and sulfonate; and R¹¹ and R¹² are each independently selected from the group consisting of H, (CH₂)$_{n''}$SO₃—, and (CH₂)$_{n''}$SO₃H, wherein n'' is 1 or 2.

17. A molecule with two pendant phenylarsine moieties according to the general structural Formula (XI):

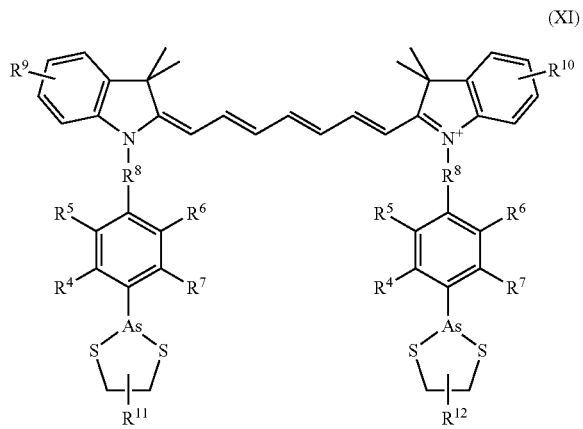

(XI)

wherein R⁴, R⁵, R⁶ and R⁷ are each independently H, F, OR³, R³, OAc, NH₂, N(C₁–C₄ alkyl)₂; or R⁴ with R⁵, or R⁶ together with R⁷, or both, form a ring; wherein R³ is H, CH(OH)CH₂OH or (CH₂)$_q$—Y, wherein q is 1–4 and Y is H, OH, NH₂, SH, COOH, OAc, CONH₂ or CN; R⁸ is a linear or branched optionally substituted spacer having a length of from approximately 1.5 to approximately 15 Ångstroms; R⁹ and R¹⁰ are each independently selected from the group consisting of H and sulfonate; and R¹¹ and R¹² are each independently selected from the group consisting of H, (CH₂)$_{n''}$SO₃—, and (CH₂)$_{n''}$SO₃H, wherein n'' is 1 or 2.

18. A kit comprising:
(a) a molecule according to Formula (I) of claim 1; and
(b) a molecule containing a target sequence, said target sequence comprising an amino acid sequence of the form: C(X)$_i$C(X)$_j$C(X)$_k$C, wherein C is cysteine, X is any amino acid, and i, j, and k are each independently 0 or an integer of from 1 to 6.

19. A kit comprising:
(a) a molecule according to Formula (I) of claim 1; and
(b) a reagent that promotes the formation of a complex between said molecule according to Formula (I) and a peptide comprising a target sequence, said target sequence comprising an amino acid sequence of the form C(X)$_i$C(X)$_j$C(X)$_k$C, wherein C is cysteine, X is any amino acid, and i, j, and k are each independently 0 or an integer of from 1 to 6.

\* \* \* \* \*

UNITED STATES PATENT AND TRADEMARK OFFICE
CERTIFICATE OF CORRECTION

PATENT NO.        : 7,141,655 B2
APPLICATION NO. : 10/461224
DATED             : November 28, 2006
INVENTOR(S)       : Ebright et al.

It is certified that error appears in the above-identified patent and that said Letters Patent is hereby corrected as shown below:

At column 6, line 59, the printed patent should read --...Z being able to participate...--.

At column 25, line 17, the printed patent should read --...and filtering away the solid...--.

At column 30, line 60, the printed patent should read --...Labeling of tagged α derivatives...--.

Signed and Sealed this

Twentieth Day of February, 2007

JON W. DUDAS
*Director of the United States Patent and Trademark Office*